United States Patent
Fujita et al.

(10) Patent No.: US 11,224,625 B2
(45) Date of Patent: Jan. 18, 2022

(54) IMMUNITY-INDUCING AGENT

(71) Applicant: TORAY INDUSTRIES, INC., Tokyo (JP)

(72) Inventors: Takayuki Fujita, Kamakura (JP); Fumiyoshi Okano, Kamakura (JP)

(73) Assignee: TORAY INDUSTRIES, INC., Tokyo (JP)

(*) Notice: Subject to any disclaimer, the term of this patent is extended or adjusted under 35 U.S.C. 154(b) by 301 days.

(21) Appl. No.: 16/084,100

(22) PCT Filed: Mar. 27, 2017

(86) PCT No.: PCT/JP2017/012269
§ 371 (c)(1),
(2) Date: Sep. 11, 2018

(87) PCT Pub. No.: WO2017/170338
PCT Pub. Date: Oct. 5, 2017

(65) Prior Publication Data
US 2019/0076492 A1    Mar. 14, 2019

(30) Foreign Application Priority Data
Mar. 28, 2016  (JP) .............................. JP2016-064032

(51) Int. Cl.
| | |
|---|---|
| *A61K 35/76* | (2015.01) |
| *A61K 39/39* | (2006.01) |
| *A61P 35/00* | (2006.01) |
| *C07K 14/54* | (2006.01) |
| *C07K 14/555* | (2006.01) |
| *C07K 14/705* | (2006.01) |
| *C07K 14/47* | (2006.01) |
| *A61K 39/00* | (2006.01) |
| *C12N 15/09* | (2006.01) |
| *C12N 15/62* | (2006.01) |

(52) U.S. Cl.
CPC .............. *A61K 35/76* (2013.01); *A61K 39/00* (2013.01); *A61K 39/001102* (2018.08); *A61K 39/39* (2013.01); *A61P 35/00* (2018.01); *C07K 14/4748* (2013.01); *C07K 14/54* (2013.01); *C07K 14/555* (2013.01); *C07K 14/705* (2013.01); *C07K 14/70596* (2013.01); *A61K 2039/53* (2013.01); *A61K 2039/55555* (2013.01); *A61K 2039/828* (2018.08); *A61K 2039/844* (2018.08); *A61K 2039/852* (2018.08); *A61K 2039/86* (2018.08); *A61K 2039/868* (2018.08); *A61K 2039/892* (2018.08); *C12N 15/09* (2013.01); *C12N 15/62* (2013.01)

(58) Field of Classification Search
CPC ............ A61K 2039/505; A61K 39/395; A61K 45/00; A61P 35/00; C07K 16/18; C07K 16/28; C07K 16/30; C07K 2317/732; C12N 15/09
See application file for complete search history.

(56) References Cited

U.S. PATENT DOCUMENTS

2011/0130343 A1    6/2011  Okano et al.

FOREIGN PATENT DOCUMENTS

| CN | 102481333 A | 5/2012 |
|---|---|---|
| EP | 2 474 315 A1 | 7/2012 |
| RU | 2 519 675 C2 | 8/2012 |
| WO | WO 03/025148 A2 | 3/2003 |
| WO | WO 2015/006437 A1 | 1/2015 |

OTHER PUBLICATIONS

Tang et al., 2003, Geneseq Accession No. ADI21156, computer printout, pp. 2-4.*
Chan, Li, MRAP2 (Melanocortin Receptor Accessory Protein Two) and its role in melanocortin receptor trafficking and expression, Queen Mary University of London, published dissertation, 2009.*
Alix A.J. Rouault, Melanocortin Receptor Accessory Proteins (MRAPs): Functions in the melanocortin system and beyond☆, BBA—Molecular Basis of Disease 1863 (2017) 2462-2467.*
David S. Jackson, Melanocortin receptor accessory proteins in adrenal disease and obesity, Front. Neurosci. 9:213, Jun. 10, 2015 .*
Chan et al., "MRAP and MRAP2 are bidirectional regulators of the melanocortin receptor family", PNAS, vol. 106, No. 15, Apr. 14, 2009, pp. 6146-6151.
Gorrigan et al., "Localisation of the melanocortin-2-receptor and its accessory proteins in the developing and adult adrenal gland", Journal of Molecular Endocrinology, vol. 46, 2011, pp. 227-232.
Hofland et al., "Melanocortin 2 Receptor-Associated Protein (MRAP) and MRAP2 in Human Adrenocortical Tissues: Regulation of Expression and Association with ACTH Responsiveness", J Clin Endocrinol Metab., vol. 97, No. 5, May 2012, pp. E747-E754.
International Search Report (PCT/ISA/210) issued in PCT/JP2017/012269, dated Jun. 27, 2017.

(Continued)

*Primary Examiner* — James H Alstrum-Acevedo
*Assistant Examiner* — Erinne R Dabkowski
(74) *Attorney, Agent, or Firm* — Birch, Stewart, Kolasch & Birch, LLP

(57) ABSTRACT

The present invention relates to a novel immunity-inducing agent for treatment and/or prevention of cancer. Specifically, the present invention relates to an immunity-inducing agent comprising, as an active ingredient, at least one polypeptide having immunity-inducing activity and selected from polypeptides derived from MRAP2 and modified forms thereof, or a recombinant vector comprising a polynucleotide encoding the polypeptide and capable of expressing the polypeptide in vivo, and a method for inducing immunity, comprising administering the immunity-inducing agent to a subject.

1 Claim, 3 Drawing Sheets

Specification includes a Sequence Listing.

(56) References Cited

OTHER PUBLICATIONS

Written Opinion (PCT/ISA/237) issued in PCT/JP2017/012269, dated Jun. 27, 2017.
Extended European Search Report dated Oct. 28, 2019, in European Patent Application No. 17774875.3.
Office Action dated Apr. 29, 2020, in Russian Patent Application No. 2018137816/14(062710).
Kobayashi, "Technique of Producing Antibody According to DNA Immunization Method," Pharmacia (2012), vol. 48, No. 4, pp. 301-304.
Office Action dated May 11, 2021, in Japanese Patent Application No. 2017-539041.
Gen Bank: AAH39855.1, Melanocortin 2 receptor accessory protein 2 [*Homo sapiens*] (Jul. 21, 2008).
NCBI Reference Sequence: NP_001094952.2, melanocortin-2 receptor accessory protein 2 [Mus musculus] (Feb. 15, 2015).
NCBI Reference Sequence: XP_003986394.1, melanocorton-2 receptor accessory protein 2 [Felis catus] (Feb. 10, 2015).
NCBI Reference Sequence: XP_005627643.1, melanocortin-2 receptor accessory protein 2 isoform X2 [Canis lupus familiaris] (Sep. 24, 2013).
Office Action dated May 17, 2021, in Chinese Patent Application No. 201780010566.4.
"unnamed protein product [*Homo sapiens*]", GenBank: BAC03517.1. Jan. 9, 2008, retrieved Jun. 15, 2021.
Office Action dated Oct. 27, 2021 for Korean Patent Application No. 10-2018-7029850.

\* cited by examiner

SEQUENCE LISTING

<160> NUMBER OF SEQ ID NOS: 20

<210> SEQ ID NO 1
<211> LENGTH: 2229
<212> TYPE: DNA
<213> ORGANISM: Homo sapiens
<220> FEATURE:
<221> NAME/KEY: CDS
<222> LOCATION: (191)..(808)

<400> SEQUENCE: 1

```
tccggcgccc cgcgccgcct ccgctgcggg tcgggagcgc gcgtctccgc cgcacctcgg      60
atctaggagc tactcgcccg gccctgggcg gtgggaggcg gcggcggcgg cggcgctcgc     120
gcacctcgga ggagccagga gccggaacca gggccgagcc cgcgggccgg ggctagccag     180
ccggtcggag atg tcc gcc cag agg tta att tct aac aga acc tcc cag       229
            Met Ser Ala Gln Arg Leu Ile Ser Asn Arg Thr Ser Gln
              1               5                  10 caa tcg gca tct aat tct gat tac acc tgg gaa tat gaa tat tat gag     277
Gln Ser Ala Ser Asn Ser Asp Tyr Thr Trp Glu Tyr Glu Tyr Tyr Glu
     15                  20                  25 att gga cca gtt tcc ttt gaa gga ctg aag gct cat aaa tat tcc att     325
Ile Gly Pro Val Ser Phe Glu Gly Leu Lys Ala His Lys Tyr Ser Ile
 30                  35                  40                  45 gtg att gga ttt tgg gtt ggt ctt gca gtc ttc gtg att ttt atg ttt     373
Val Ile Gly Phe Trp Val Gly Leu Ala Val Phe Val Ile Phe Met Phe
                 50                  55                  60 ttt gtg ctg acc ttg ctg acc aag aca gga gcc cca cac caa gac aat     421
Phe Val Leu Thr Leu Leu Thr Lys Thr Gly Ala Pro His Gln Asp Asn
                     65                  70                  75 gca gag tcc tca gag aag aga ttc aga atg aac agc ttt gtg tca gac     469
Ala Glu Ser Ser Glu Lys Arg Phe Arg Met Asn Ser Phe Val Ser Asp
             80                  85                  90 ttt gga aga cct ctg gag cca gat aaa gta ttt tct cgc caa ggc aac     517
Phe Gly Arg Pro Leu Glu Pro Asp Lys Val Phe Ser Arg Gln Gly Asn
         95                  100                 105 gag gag tcc agg tct ctc ttt cac tgc tac atc aat gag gtg gaa cgc     565
Glu Glu Ser Arg Ser Leu Phe His Cys Tyr Ile Asn Glu Val Glu Arg
 110                 115                 120                 125 ttg gac aga gcc aaa gct tgt cac cag acc aca gcc ctt gac agt gac     613
Leu Asp Arg Ala Lys Ala Cys His Gln Thr Thr Ala Leu Asp Ser Asp
                 130                 135                 140 gtc caa ctc cag gaa gcc atc aga agc agt ggg cag cca gag gag gag     661
Val Gln Leu Gln Glu Ala Ile Arg Ser Ser Gly Gln Pro Glu Glu Glu
             145                 150                 155 ctg aac agg ctc atg aag ttt gac atc ccc aac ttt gtg aac aca gac     709
Leu Asn Arg Leu Met Lys Phe Asp Ile Pro Asn Phe Val Asn Thr Asp
         160                 165                 170 cag aac tac ttt ggg gag gat gat ctt ctg att tct gaa cca cct att     757
Gln Asn Tyr Phe Gly Glu Asp Asp Leu Leu Ile Ser Glu Pro Pro Ile
     175                 180                 185 gtt ctg gaa act aag cca ctt tcc cag acc tca cac aaa gac ctg gat     805
Val Leu Glu Thr Lys Pro Leu Ser Gln Thr Ser His Lys Asp Leu Asp
 190                 195                 200                 205 tga gaaacatgct ctgtaaaggg tcttcctgaa gatgtggatt ctatctttat          858
gtagcaagaa atctacatcc accaaaattg tgtgtgtttg ggggagagag agacatagag    918
atagagacag agaggcagag aagagacccc tttagaagag agctgagctg attaagctga    978
gtggtttttt gttttgtttt gttttgtgctt tttaatacat ttggagcttt gggagtatta   1038
```

```
aagtatttac accaagcttg tccaacccgt ggcatgtgtc ccaggacagc tttgaatgtg   1098
gcccaataca aatttaaac tttattaaaa catgagtttt gttttttttt ttgctatttt   1158
ttttaaagct cgtcagctat cgttagtgtt agtgtacttt atgtgtggcc caagacaact   1218
cttcttccag tgtggcacag ggaagctaaa agattggaca cctctgattt atactagctc   1278
gttttgcttg ttgaaaaatt tggccaaata cctattgtca gcattcttgg gtgaggatta   1338
gcctaccatg ttctaatctg gccctgccac tactatgctc tacctttggt gagttgcttt   1398
acctctctgg gctgccccat ttttaactgt aggttgacag gtctagagtg atccatccca   1458
cctctaatat tttgtgaatt tatgactttg ccttcagatg aggctgagct atacataaaa   1518
cagtataaac tagggtactg cctcgtatct cttgtaggct ctctcaaatc tctgtaccct   1578
ccacttaacc ctaattgagc caagctttag tcagggatc tggttgtcta ccagaatgtc   1638
aggagactca tcttacacag tcatggtggc caatgtttct ggtgggttgt gctgaaacag   1698
ctcttctgag aacttccaac cacccatgct ctaacctgga gacagccatc ccctgcctca   1758
gaataagtac caattcgtag tacatgtatg gtactcttgt ccccaagaaa tgttaggaag   1818
cttgtcagct gaatgagagg aggtgccttc tgggtatctc tgtgttggtg tatctgtgcc   1878
attggctaca gaacaagaaa aatactattt gccatgctat taccttggca gatgtgtagg   1938
tgatagtcat ctggctttga gctgagatgg tcagtgggtt gtaaattccc cactagcaga   1998
tattcagggt ggcctgagtt atgtaaacaa gtgagcaaca cagctttaat ttcatggagg   2058
aatcaaagct gcacactggt attaaaacaa cttgatttg cgcacacagt gcatgcatg   2118 gcaagctgtt aacctctggg tggcattttc attatgaatt tgttcaccac ctgtcttgct   2178
taagctacaa aataaatgca tttgactgca cagaaaaaaa aaaaaaaaa a            2229
```

<210> SEQ ID NO 2
<211> LENGTH: 205
<212> TYPE: PRT
<213> ORGANISM: Homo sapiens

<400> SEQUENCE: 2

```
Met Ser Ala Gln Arg Leu Ile Ser Asn Arg Thr Ser Gln Gln Ser Ala
1               5                   10                  15

Ser Asn Ser Asp Tyr Thr Trp Glu Tyr Glu Tyr Tyr Glu Ile Gly Pro
            20                  25                  30

Val Ser Phe Glu Gly Leu Lys Ala His Lys Tyr Ser Ile Val Ile Gly
        35                  40                  45

Phe Trp Val Gly Leu Ala Val Phe Val Ile Phe Met Phe Phe Val Leu
    50                  55                  60

Thr Leu Leu Thr Lys Thr Gly Ala Pro His Gln Asp Asn Ala Glu Ser
65                  70                  75                  80

Ser Glu Lys Arg Phe Arg Met Asn Ser Phe Val Ser Asp Phe Gly Arg
                85                  90                  95

Pro Leu Glu Pro Asp Lys Val Phe Ser Arg Gln Gly Asn Glu Glu Ser
            100                 105                 110

Arg Ser Leu Phe His Cys Tyr Ile Asn Glu Val Glu Arg Leu Asp Arg
        115                 120                 125

Ala Lys Ala Cys His Gln Thr Thr Ala Leu Asp Ser Asp Val Gln Leu
    130                 135                 140

Gln Glu Ala Ile Arg Ser Ser Gly Gln Pro Glu Glu Leu Asn Arg
145                 150                 155                 160

Leu Met Lys Phe Asp Ile Pro Asn Phe Val Asn Thr Asp Gln Asn Tyr
```

```
                    165                 170                 175
Phe Gly Glu Asp Asp Leu Leu Ile Ser Glu Pro Pro Ile Val Leu Glu
            180                 185                 190

Thr Lys Pro Leu Ser Gln Thr Ser His Lys Asp Leu Asp
        195                 200                 205

<210> SEQ ID NO 3
<211> LENGTH: 1967
<212> TYPE: DNA
<213> ORGANISM: Canis familiaris
<220> FEATURE:
<221> NAME/KEY: CDS
<222> LOCATION: (175)..(795)

<400> SEQUENCE: 3
tatgtaagcc attttagtca gctgtcatgt gaatgcaggg gacagaggcg atgtaatgcg      60
cacccacgta agagtatctg cttgctatga agatgtggat gtcagactgc taactttctt     120
gcagaggacc actgttactg cgaggttatc tcttcctcac ttagaagggt ggag atg       177
                                                             Met
                                                             1 tct gcc cag aga tta att tct aac aga aca tcc cag cca tct gca cct       225
Ser Ala Gln Arg Leu Ile Ser Asn Arg Thr Ser Gln Pro Ser Ala Pro
          5                  10                  15 aat tct gat tac acc tgg gaa tat gaa tat tat gaa att gga cca gtg       273
Asn Ser Asp Tyr Thr Trp Glu Tyr Glu Tyr Tyr Glu Ile Gly Pro Val
         20                  25                  30 tcc ttt gaa gga ctg aag gct cat aaa tat tcc att gtg att gga ttt       321
Ser Phe Glu Gly Leu Lys Ala His Lys Tyr Ser Ile Val Ile Gly Phe
 35                  40                  45 tgg gtt ggt ctc gct gtc ttt gtg att ttc atg ttt ttt gtg ctg act       369
Trp Val Gly Leu Ala Val Phe Val Ile Phe Met Phe Phe Val Leu Thr
 50                  55                  60                  65 ttg ctg acc aag acg gga gct cca cac caa gac aat gca gaa tct tca       417
Leu Leu Thr Lys Thr Gly Ala Pro His Gln Asp Asn Ala Glu Ser Ser
                 70                  75                  80 gag aag aga ttt aga atg aat agc ttt gtg tca gac ttt gga aga cca       465
Glu Lys Arg Phe Arg Met Asn Ser Phe Val Ser Asp Phe Gly Arg Pro
             85                  90                  95 ctg gag cca gat aag gtg ttt tct cga cag ggc aat gat gaa tcc agg       513
Leu Glu Pro Asp Lys Val Phe Ser Arg Gln Gly Asn Asp Glu Ser Arg
        100                 105                 110 tct ctc ttt cat tgc tac atc aat gaa gtg gaa cac ttg gat agg gct       561
Ser Leu Phe His Cys Tyr Ile Asn Glu Val Glu His Leu Asp Arg Ala
    115                 120                 125 aaa gtt tgt cat cag acc acg gtc ctt gac agc agt gtt cga ctc cag       609
Lys Val Cys His Gln Thr Thr Val Leu Asp Ser Ser Val Arg Leu Gln
130                 135                 140                 145 gaa gcc att aga agc aat ggg cgt cca gag gag gag ctg aat agg ctt       657
Glu Ala Ile Arg Ser Asn Gly Arg Pro Glu Glu Glu Leu Asn Arg Leu
                150                 155                 160 atg aag ttt gat atc cct aac ttt gtg aat aca gac cag aac tcc tcc       705
Met Lys Phe Asp Ile Pro Asn Phe Val Asn Thr Asp Gln Asn Ser Ser
            165                 170                 175 ttt ggg gag gat gat ctt cta att tca gaa cca cct att gtt cta gaa       753
Phe Gly Glu Asp Asp Leu Leu Ile Ser Glu Pro Pro Ile Val Leu Glu
        180                 185                 190 aat aag cca gtt tcc cag acc tca cac aaa gac ctg gat tga              795
Asn Lys Pro Val Ser Gln Thr Ser His Lys Asp Leu Asp
    195                 200                 205
```

```
gaaactactc tgtaaagtgt cttcctgaag atgttgggtc tgtctttgta aagcaagaaa      855
tctccattca ccaagattgt gtgtatgtgt gtgtgggggg gtagctaagt gggggtgtta      915
tgagagatag aaacagagga gagagccccc tcaaaaacga gccgaataag ctgagtttct      975
atgcctttaa acacagttca ggcttttttgg ggataaggt acttatatgg tttcatcctc     1035
ttcgttgttg aaaaatttgg ccacatactc agtgtcaacg ttcttgaatg ggggttagca     1095
tactgtgttc cagtctggcc ctgccaattc catgctctac ctttagcaag ttgctttacc     1155
tctctgggct gccacattgt taaccgtaac atggggagtc tggagtagat tattcatcct     1215
agctctaata ttttgtgaac ttgtgacttt gcatcgagaa gaggctgggt tatatgtaaa     1275
tcaatataaa ctatggcact gcctcctatc tcttgtagga tccccatgt cagtaccttc      1335
cactcaacct taactgagcc cagcttttgt caagggtcca agcatctaga ggatgtcaga     1395
cgactcacct cacagtcacc gtggccaaca tttctgttgg ttgtatgaaa atagctcttc     1455
tgagaacctc cagccaccca tggtaaaacg tagggacagc catgcccctc ctcttctaga     1515
atgagtacca atccatgata cattgcatgg cactcctatc cccagaaatg tagggaaggt     1575
tgtcagctga gtgatgacag gtgcctttttg tgtctctgtt ggtgaacatg tgtctggtca    1635
catttctgtg tggttggcta ctgaacaaga aaagtgccat ttgccatgct ctttacttgg     1695
taggggtgta ggtgatggtc atgtggctcg tgtgtgggct ttgagctgag gtggtgaatg     1755
gattgtaaat tccccaccaa cagatgtgca gggtggcctg gtgcaacaca gttaatttcc     1815
cgaaggaatc tagtcctggt attgggaaaa acttggtctt gcatacacag ttgcatgtgc     1875
agccagctgc taatctctgg gtggcatttt cattatgaat ttgttcacca tctgtcttgc     1935
ttaagcaaaa aaaataaatg catttgattg ca                                    1967

<210> SEQ ID NO 4
<211> LENGTH: 206
<212> TYPE: PRT
<213> ORGANISM: Canis familiaris

<400> SEQUENCE: 4

Met Ser Ala Gln Arg Leu Ile Ser Asn Arg Thr Ser Gln Pro Ser Ala
1               5                   10                  15

Pro Asn Ser Asp Tyr Thr Trp Glu Tyr Glu Tyr Glu Ile Gly Pro
            20                  25                  30

Val Ser Phe Glu Gly Leu Lys Ala His Lys Tyr Ser Ile Val Ile Gly
        35                  40                  45

Phe Trp Val Gly Leu Ala Val Phe Val Ile Phe Met Phe Phe Val Leu
    50                  55                  60

Thr Leu Leu Thr Lys Thr Gly Ala Pro His Gln Asp Asn Ala Glu Ser
65                  70                  75                  80

Ser Glu Lys Arg Phe Arg Met Asn Ser Phe Val Ser Asp Phe Gly Arg
                85                  90                  95

Pro Leu Glu Pro Asp Lys Val Phe Ser Arg Gln Gly Asn Asp Glu Ser
            100                 105                 110

Arg Ser Leu Phe His Cys Tyr Ile Asn Glu Val Glu His Leu Asp Arg
        115                 120                 125

Ala Lys Val Cys His Gln Thr Thr Val Leu Asp Ser Val Arg Leu
    130                 135                 140

Gln Glu Ala Ile Arg Ser Asn Gly Arg Pro Glu Glu Leu Asn Arg
145                 150                 155                 160

Leu Met Lys Phe Asp Ile Pro Asn Phe Val Asn Thr Asp Gln Asn Ser
```

```
                          165                 170                 175
Ser Phe Gly Glu Asp Asp Leu Leu Ile Ser Glu Pro Pro Ile Val Leu
                180                 185                 190

Glu Asn Lys Pro Val Ser Gln Thr Ser His Lys Asp Leu Asp
            195                 200                 205

<210> SEQ ID NO 5
<211> LENGTH: 1849
<212> TYPE: DNA
<213> ORGANISM: Felis catus
<220> FEATURE:
<221> NAME/KEY: CDS
<222> LOCATION: (72)..(692)

<400> SEQUENCE: 5
gaggcggtgg cgaagctcac gcacctcgga ggagcggtgc ccgcgggccg gggagcgcca        60
gccgggtaga g atg tct gcc cag agg tta att tct aac aga aca tcc cag       110
             Met Ser Ala Gln Arg Leu Ile Ser Asn Arg Thr Ser Gln
               1               5                  10 caa tct gca tct aat tct gat tac acc tgg gaa tat gaa tat tat gag       158
Gln Ser Ala Ser Asn Ser Asp Tyr Thr Trp Glu Tyr Glu Tyr Tyr Glu
 15              20                  25 att gga cca gtt tcc ttt gaa gga ctg aag gct cat aaa tat tcc att       206
Ile Gly Pro Val Ser Phe Glu Gly Leu Lys Ala His Lys Tyr Ser Ile
 30              35                  40                  45 gtg att gga ttt tgg gtt ggt ctt gct gtc ttc gtg att ttc atg ttt       254
Val Ile Gly Phe Trp Val Gly Leu Ala Val Phe Val Ile Phe Met Phe
                 50                  55                  60 ttt gtg ctg act ttg ctg acc aag acg gga gct cca cac caa gac aat       302
Phe Val Leu Thr Leu Leu Thr Lys Thr Gly Ala Pro His Gln Asp Asn
                     65                  70                  75 gca gag tct tca gag aag aga ttc aga atg aat agc ttt gtg tca gac       350
Ala Glu Ser Ser Glu Lys Arg Phe Arg Met Asn Ser Phe Val Ser Asp
             80                  85                  90 ttc gga aga cca ctg gag cca gat aag gtg ttt tct cga cag ggc aat       398
Phe Gly Arg Pro Leu Glu Pro Asp Lys Val Phe Ser Arg Gln Gly Asn
 95                 100                 105 gag gaa tcc agg tct ctc ttt cac tgc tac atc aac gaa gtg gaa cac       446
Glu Glu Ser Arg Ser Leu Phe His Cys Tyr Ile Asn Glu Val Glu His
110                 115                 120                 125 ttg gat agg gct aaa gct tgt cag cag acc aca gcc ctt gac agc tgt       494
Leu Asp Arg Ala Lys Ala Cys Gln Gln Thr Thr Ala Leu Asp Ser Cys
                130                 135                 140 gtt caa ctg cag gaa gcc att aga agc aac ggg cgg cca gag gag gag       542
Val Gln Leu Gln Glu Ala Ile Arg Ser Asn Gly Arg Pro Glu Glu Glu
            145                 150                 155 ttg aac agg ctc atg aag ttt gac atc ccc aac ttc gtg aac aca gac       590
Leu Asn Arg Leu Met Lys Phe Asp Ile Pro Asn Phe Val Asn Thr Asp
        160                 165                 170 cag aac tcc tcc ttt ggg gag gat gat ctt ctg att tca gaa cca cct       638
Gln Asn Ser Ser Phe Gly Glu Asp Asp Leu Leu Ile Ser Glu Pro Pro
    175                 180                 185 att gtt cta gaa aat aag cca gtt tcc cag acg tca cac aaa gac ctg       686
Ile Val Leu Glu Asn Lys Pro Val Ser Gln Thr Ser His Lys Asp Leu
190                 195                 200                 205 gat tga gaaacgtact ctgtaaagtg tcttcctgga gatgttggat ccgtctttgt       742
Asp aaagcaagaa atctccactg accacagttg tttgtgtgtg ttggggggga gacatgggag      802
acagagatag aaagaaagac acagagaaga gagcccccte agaaaagagc tgaagaagct      862
```

-continued

```
gagtttctgt gcctttaaac acagttcagg ctttttttgag aataaagtat ttgcatggtc    922
tcatctttct tgttgttgaa aagtttggct gcacagagtg tcagtgttct tgaatggggg    982
ttagcatgct gcattccagt ctggccctgc caccaccacg ctctattttt agcaagttgc   1042
tttacctctc tgggctgcca cattgttcat tgtaacatga ggagtttgaa gtagatgact   1102
catcccagct ctaatatttt gtgaatttgt gactttgcat ccagaagaag ctggaatgta   1162
cataatgcag tataaaccag ggcactgcct cctatctctt gtaggatgcc ctatgttggt   1222
accttccact cagcccttaa ctgagcccag cttttgtcag aggtccaagc atctatgagg   1282
aggtcagaag acacatctct cagtcaccat ggccaacatt tctttgattg tactgaaaaa   1342
gctcttctga gaacctccag ccacccatgc taaaagctag ggccagccct gcccctcttc   1402
tcccagaatg aaccaattca tggtaccaat tcatggtaca tcgcatggca ctcttgttcc   1462
cagaaatgta gagaaggttg tcagctcagt gagaggaggt gccttttgta tctctgtgtt   1522
ggcgtgcgtc cgtcacaaga agagtacttg ccatgctatt tacttggcag atgtgtaggt   1582
gatagtcatg tgactcgtgt atggactttg agctgagatg gtgaatgggt tgtaaatccc   1642
caccaacaga tatgcagggt ggcctggtgc aacacagagt taatttcatg aaagaatcca   1702
gtctgcacac tggtattgga aacaacttgg ttttgcgcac acagttgctt gcatggccaa   1762
ctgctaatct ctgggtggca ttttcatcat gagtttgttt accacctgtc ttgctaaagc   1822
taaaaaataa atgcatttgc acaggaa                                       1849
```

<210> SEQ ID NO 6
<211> LENGTH: 206
<212> TYPE: PRT
<213> ORGANISM: Felis catus

<400> SEQUENCE: 6

```
Met Ser Ala Gln Arg Leu Ile Ser Asn Arg Thr Ser Gln Gln Ser Ala
1               5                   10                  15

Ser Asn Ser Asp Tyr Thr Trp Glu Tyr Glu Tyr Glu Ile Gly Pro
            20                  25                  30

Val Ser Phe Glu Gly Leu Lys Ala His Lys Tyr Ser Ile Val Ile Gly
        35                  40                  45

Phe Trp Val Gly Leu Ala Val Phe Val Ile Phe Met Phe Phe Val Leu
    50                  55                  60

Thr Leu Leu Thr Lys Thr Gly Ala Pro His Gln Asp Asn Ala Glu Ser
65                  70                  75                  80

Ser Glu Lys Arg Phe Arg Met Asn Ser Phe Val Ser Asp Phe Gly Arg
                85                  90                  95

Pro Leu Glu Pro Asp Lys Val Phe Ser Arg Gln Gly Asn Glu Glu Ser
            100                 105                 110

Arg Ser Leu Phe His Cys Tyr Ile Asn Glu Val Glu His Leu Asp Arg
        115                 120                 125

Ala Lys Ala Cys Gln Gln Thr Thr Ala Leu Asp Ser Cys Val Gln Leu
    130                 135                 140

Gln Glu Ala Ile Arg Ser Asn Gly Arg Pro Glu Glu Leu Asn Arg
145                 150                 155                 160

Leu Met Lys Phe Asp Ile Pro Asn Phe Val Asn Thr Asp Gln Asn Ser
                165                 170                 175

Ser Phe Gly Glu Asp Asp Leu Leu Ile Ser Glu Pro Pro Ile Val Leu
            180                 185                 190
```

```
Glu Asn Lys Pro Val Ser Gln Thr Ser His Lys Asp Leu Asp
        195                 200                 205

<210> SEQ ID NO 7
<211> LENGTH: 1948
<212> TYPE: DNA
<213> ORGANISM: Mus musculus
<220> FEATURE:
<221> NAME/KEY: CDS
<222> LOCATION: (94)..(717)

<400> SEQUENCE: 7
gttcactggc ggcggcggca cggcggcggt gaggctcgag caccggagga gctgaaccgt      60
gtaaagcctg cggtaaccca ggacaggacg ggg atg gag atg tct gcc cag agg     114
                                    Met Glu Met Ser Ala Gln Arg
                                     1               5 ctg gct tct aac agg aca tcc cca cag tca cca tcg aac tct gac tac     162
Leu Ala Ser Asn Arg Thr Ser Pro Gln Ser Pro Ser Asn Ser Asp Tyr
         10                  15                  20 acc tgg gaa tac gag tac tat gag atc gga cca gtt tcc ttt gaa gga     210
Thr Trp Glu Tyr Glu Tyr Tyr Glu Ile Gly Pro Val Ser Phe Glu Gly
 25                  30                  35 ctg aag gct cat aaa tat tcc att gtg att gga ttc tgg gtt ggt ctt     258
Leu Lys Ala His Lys Tyr Ser Ile Val Ile Gly Phe Trp Val Gly Leu
 40                  45                  50                  55 gcg gtc ttt gtg att ttc atg ttt ttt gtg ctg act ttg ctg acg aag     306
Ala Val Phe Val Ile Phe Met Phe Phe Val Leu Thr Leu Leu Thr Lys
                 60                  65                  70 aca ggt gcc cca cac caa gac aac gcg gag tcc tca gag agg agg ttc     354
Thr Gly Ala Pro His Gln Asp Asn Ala Glu Ser Ser Glu Arg Arg Phe
             75                  80                  85 cgc atg aac agc ttt gtg tca gac ttc ggg aag ccg ctg gag tca gac     402
Arg Met Asn Ser Phe Val Ser Asp Phe Gly Lys Pro Leu Glu Ser Asp
         90                  95                 100 aag gtg ttt tct cgt cag ggc aac gag gag tcc agg tct ctg ttc cac     450
Lys Val Phe Ser Arg Gln Gly Asn Glu Glu Ser Arg Ser Leu Phe His
     105                 110                 115 tgt tac atc aat gaa gta gaa cac ttg gac agg gtt aaa gtt tgc cac     498
Cys Tyr Ile Asn Glu Val Glu His Leu Asp Arg Val Lys Val Cys His
120                 125                 130                 135 caa aca aca gcc atc gac agt gat gtc cac ctc cag gaa gcc agc aga     546
Gln Thr Thr Ala Ile Asp Ser Asp Val His Leu Gln Glu Ala Ser Arg
                140                 145                 150 agc agt ggg agg cct gag gag gag cta gcc agg ttc atg aag ttt gac     594
Ser Ser Gly Arg Pro Glu Glu Glu Leu Ala Arg Phe Met Lys Phe Asp
            155                 160                 165 atc ccc aac ttt gtg aac aca gag cag agc tcc ttt ggg gag gat gat     642
Ile Pro Asn Phe Val Asn Thr Glu Gln Ser Ser Phe Gly Glu Asp Asp
        170                 175                 180 ctc ctg att tcg gaa gca ccc gtt ctt cta gaa aac aag cca gtt tcc     690
Leu Leu Ile Ser Glu Ala Pro Val Leu Leu Glu Asn Lys Pro Val Ser
    185                 190                 195 cag aca tca cgc ata gac ctg gac tga gagacacttg tgccttactg             737
Gln Thr Ser Arg Ile Asp Leu Asp
200                 205 aggatgtgtt ctgtctctgt acagcaagaa accgcaagct acccacactc gtgtgtgtgt    797
gtgtgtgtgt gtgtgtgtgt gtgtgtgtag agagagagag agagagagag agagagagag    857
agagagagag gaggtgaggg aggggagag gactaggcta ggactgggat gtgatagagg     917
ggcagaattt ggagatggaa ggcaccattt tggtttgggg gagatgatat ttttctttt     977
```

```
tggattaaaa aaatgcattg acagtattaa ggcttcttta ttgaaacaat tagccacata    1037
tatgcaattg agcccctcc tgggtgaggg ttaggttact gcagtctgat ctagcccttt    1097
cccaccattc tctgcctgta acaagttgct ttacctctct ggactgccat ggttttacat    1157
gtaaggtggc ctgtctggag tagatgacct atcccagctc tagaattttt gtggctttca    1217
gacttagcgt ttaagacatg ctaagaaaca cataaacagt agataataga acatggcacc    1277
ctggctttca gggcaggttc tccagggctt ggtaccctcc ctttgctcag cccttcacag    1337
agtctcactt tagctaggga aacctttacc aggagcacag gagcctcaca tgcactgtgg    1397
acagtgtctc tgcgagtttt gccgcagcag tttatgtgat gaactccacc cacccccggct    1457 ttaaactggg gcagctttga ctccagtgag taccagccta aactgtttca caagcatccg    1517
tgctctcaaa aactgctagg gcagattgtc atctgcctga tgtgggtccc ttctcggtgt    1577
ctccgagttt gcatcctgtg ctcgcgcttc tgaactcttt ggcttcagaa caagacgctc    1637
cttgccatgg tctgcgtggc agatgtgtgg gtgtcggctg cctggcttgg agctgagagg    1697
gtcagtgggt tgtttgtgcc acagtagcag atgttcagga ttgcgatgat aatttgagca    1757
acatgatgtt catttcgtgg aggaagcaac cctttgctgg tgtcggaaag aactcagcct    1817
tgcacacaga gagttgtatg catgagcagc tgctaatcga tgggtggcat ctactttacg    1877
aatttgttca ccctttgtct tgcttaagtt gcataataaa tgcatttgat cgcaaaaaaa    1937 aaaaaaaaa a                                                         1948
```

<210> SEQ ID NO 8
<211> LENGTH: 207
<212> TYPE: PRT
<213> ORGANISM: Mus musculus

<400> SEQUENCE: 8

```
Met Glu Met Ser Ala Gln Arg Leu Ala Ser Asn Arg Thr Ser Pro Gln
1               5                   10                  15

Ser Pro Ser Asn Ser Asp Tyr Thr Trp Glu Tyr Glu Tyr Tyr Glu Ile
                20                  25                  30

Gly Pro Val Ser Phe Glu Gly Leu Lys Ala His Lys Tyr Ser Ile Val
            35                  40                  45

Ile Gly Phe Trp Val Gly Leu Ala Val Phe Val Ile Phe Met Phe Phe
        50                  55                  60

Val Leu Thr Leu Leu Thr Lys Thr Gly Ala Pro His Gln Asp Asn Ala
65                  70                  75                  80

Glu Ser Ser Glu Arg Arg Phe Arg Met Asn Ser Phe Val Ser Asp Phe
                85                  90                  95

Gly Lys Pro Leu Glu Ser Asp Lys Val Phe Ser Arg Gln Gly Asn Glu
            100                 105                 110

Glu Ser Arg Ser Leu Phe His Cys Tyr Ile Asn Glu Val Glu His Leu
        115                 120                 125

Asp Arg Val Lys Val Cys His Gln Thr Thr Ala Ile Asp Ser Asp Val
130                 135                 140

His Leu Gln Glu Ala Ser Arg Ser Ser Gly Arg Pro Glu Glu Glu Leu
145                 150                 155                 160

Ala Arg Phe Met Lys Phe Asp Ile Pro Asn Phe Val Asn Thr Glu Gln
                165                 170                 175

Ser Ser Phe Gly Glu Asp Asp Leu Leu Ile Ser Glu Ala Pro Val Leu
            180                 185                 190
```

```
Leu Glu Asn Lys Pro Val Ser Gln Thr Ser Arg Ile Asp Leu Asp
        195                 200                 205
```

<210> SEQ ID NO 9
<211> LENGTH: 20
<212> TYPE: DNA
<213> ORGANISM: Artificial
<220> FEATURE:
<223> OTHER INFORMATION: T3 primer

<400> SEQUENCE: 9 aattaacccct cactaaaggg                                         20

<210> SEQ ID NO 10
<211> LENGTH: 19
<212> TYPE: DNA
<213> ORGANISM: Artificial
<220> FEATURE:
<223> OTHER INFORMATION: T7 primer

<400> SEQUENCE: 10
taatacgact cactatagg                                           19

<210> SEQ ID NO 11
<211> LENGTH: 22
<212> TYPE: DNA
<213> ORGANISM: Artificial
<220> FEATURE:
<223> OTHER INFORMATION: canis RT primer sense

<400> SEQUENCE: 11
tcgacagggc aatgatgaat cc                                       22

<210> SEQ ID NO 12
<211> LENGTH: 21
<212> TYPE: DNA
<213> ORGANISM: Artificial
<220> FEATURE:
<223> OTHER INFORMATION: canis RT primer antisense

<400> SEQUENCE: 12
tggacgccca ttgcttctaa t                                        21

<210> SEQ ID NO 13
<211> LENGTH: 22
<212> TYPE: DNA
<213> ORGANISM: Artificial
<220> FEATURE:
<223> OTHER INFORMATION: human RT primer sense

<400> SEQUENCE: 13
ttgggttggt cttgcagtct tc                                       22

<210> SEQ ID NO 14
<211> LENGTH: 21
<212> TYPE: DNA
<213> ORGANISM: Artificial
<220> FEATURE:
<223> OTHER INFORMATION: human RT primer antisense

<400> SEQUENCE: 14
tccaagcgtt ccacctcatt g                                        21

<210> SEQ ID NO 15
<211> LENGTH: 20
<212> TYPE: DNA

```
<213> ORGANISM: Artificial
<220> FEATURE:
<223> OTHER INFORMATION: mouse RT primer sense

<400> SEQUENCE: 15
ctccaggaag ccagcagaag                                               20

<210> SEQ ID NO 16
<211> LENGTH: 21
<212> TYPE: DNA
<213> ORGANISM: Artificial
<220> FEATURE:
<223> OTHER INFORMATION: mouse RT primer antisense

<400> SEQUENCE: 16
caaaggagct ctgctctgtg t                                             21

<210> SEQ ID NO 17
<211> LENGTH: 35
<212> TYPE: DNA
<213> ORGANISM: Artificial
<220> FEATURE:
<223> OTHER INFORMATION: mouse mrap2 EcoRI primer sense

<400> SEQUENCE: 17
gaattcgccg ccaccatgga gatgtctgcc cagag                              35

<210> SEQ ID NO 18
<211> LENGTH: 28
<212> TYPE: DNA
<213> ORGANISM: Artificial
<220> FEATURE:
<223> OTHER INFORMATION: mouse mrap2 NotI primer antisense

<400> SEQUENCE: 18
gcggccgctc agtccaggtc tatgcgtg                                      28

<210> SEQ ID NO 19
<211> LENGTH: 35
<212> TYPE: DNA
<213> ORGANISM: Artificial
<220> FEATURE:
<223> OTHER INFORMATION: human MRAP2 EcoRI primer sense

<400> SEQUENCE: 19
gaattcgccg ccaccatgtc cgcccagagg ttaat                              35

<210> SEQ ID NO 20
<211> LENGTH: 31
<212> TYPE: DNA
<213> ORGANISM: Artificial
<220> FEATURE:
<223> OTHER INFORMATION: human MRAP2 NotI primer antisense

<400> SEQUENCE: 20
gcggccgctc aatccaggtc tttgtgtgag g                                  31
```

IMMUNITY-INDUCING AGENT

TECHNICAL FIELD

The present vention relates to a novel immunity-inducing agent that is useful as a therapeutic and/or preventive agent for cancers, and the like.

BACKGROUND ART

Cancer is the overall leading cause of death. At present, the primary form of cancer treatment technique is surgical treatment, which is carried out in combination with radiation treatment and chemotherapy. In spite of the development of novel surgical techniques and the discovery of novel anti-cancer agents of recent years, outcomes from cancer treatment still remain unimproved, except in the cases of some types of cancers. In recent years, for example, cancer antigens recognized by cytotoxic T cells that are reactive to cancer and genes encoding cancer antigens have been identified along with the development of molecular biology and cancer immunology, and expectations for antigen-specific immunotherapy have increased.

Melanocortin 2 receptor accessory protein 2 (MRAP2) is a type 1 or type 2 transmembrane protein, and the protein participates in the control of melanocortin receptor (MCR) activity and functions in energy metabolism in vivo (Non Patent Literature 1). Also, it has been reported that MRAP2-deficient mice become obese in spite of the absence of overeating, and it has also been reported as to humans that some severely obese patients have a mutation in the MRAP2 gene (Non Patent Literature 2). However, there have been no reports that the MRAP2 protein has an immunity-inducing activity against cancer cells and thus is useful for treating and preventing cancers.

PRIOR ART LITERATURES

Non Patent Literatures

Non Patent Literature 1: Jackson D S. et al. Front. Neurosci, 9:213(2015)
Non Patent Literature 2: Asai M. et al. Science, 341:275-278(2013)

SUMMARY OF INVENTION

Problem to be Solved by the Invention

It, is an object of the present invention to find a novel polypeptide useful as a therapeutic and/or preventive agent for cancer, and the like and to provide use of such polypeptide as an immunity-inducing agent.

Means for Solving the Problem

The present inventors conducted intensive studies, and as a result, have now obtained a cDNA encoding a protein binding to an antibody present in sera from cancer-bearing living bodies by the SEREX method using a cDNA library derived from the canine testis along with sera of dogs with leukemia. Based on the cDNA, the present inventors prepared a polypeptide of canine Melanocortin 2 receptor accessory protein 2 (hereinafter referred to as MRAP2) having the amino acid sequence represented by SEQ ID NO: 4. Furthermore, based on human, cat and mouse homologous genes to the obtained canine gene, the present inventors prepared human, cat and mouse MRAP2 polypeptides having the amino acid sequences represented by SEQ ID NOs: 2, 6, and 8. The present inventors have now found that these MRAP2 polypeptides are expressed in leukemia, malignant lymphoma, lung cancer, brain tumor, colon cancer, melanoma, neuroblastoma, pancreatic cancer, stomach cancer, liver cancer, ovarian cancer, esophageal cancer, kidney cancer, mastocytoma, and perianal adenocarcinoma. Furthermore, the present inventors have now further found that immune cells against MRAP2 can be induced in vivo by administering these MRAP2 to living bodies, and that the size of a tumor in the living bodies where MRAP2 is expressed can be reduced. Moreover, they have now found that a recombinant vector capable of expressing a polynucleotide encoding MRAP2 polypeptide or a fragment thereof induces an antitumor effect on an MRAP2 expressing cancer in vivo.

The present inventors have now also found that the MRAP2 polypeptide is presented by an antigen-presenting cell and has an ability (also referred to as "immunity-inducing activity") to activate and proliferate a cytotoxic T cell specific to the polypeptide; that the polypeptide is useful for treating and/or preventing cancers because of the ability; and that the antigen-presenting cell, which was in contact with the polypeptide, and the T cell, which was in contact with the antigen-presenting cell, are useful for treating and/or preventing cancers. Based on the findings, the present invention was accomplished.

Accordingly, the present invention encompasses the following aspects:

(1) An immunity-inducing agent comprising, as an active ingredient, at least one polypeptide having immunity-inducing activity and selected from the group consisting of the following polypeptides (a) to (d), or a recombinant vector comprising a polynucleotide encoding the polypeptide and capable of expressing said polypeptide in vivo:

(a) a polypeptide consisting of 7 or more consecutive amino acids or a full-length sequence in the amino acid sequence represented by SEQ ID NO: 2, 4, 6, or 8 in the Sequence Listing;

(b) a polypeptide consisting of an amino acid sequence obtained by deletion, substitution or addition of one or several amino acids in the amino acid sequence represented by SEQ ID NO: 2, 4, 6, or 8 in the Sequence Listing;

(c) a polypeptide consisting of an amino acid sequence having a sequence identity of 90% or more with the amino acid sequence represented by SEQ ID NO: 2, 4, 6, or 8 in the Sequence Listing;

(d) a polypeptide comprising any of the polypeptides (a) to (c) as a partial sequence.

(2) The immunity-inducing agent according to (1), which is an agent for treating antigen-presenting cells.

(3) The immunity-inducing agent according to (1), which is an active ingredient for a therapeutic and/or preventing agent for cancer.

(4) The immunity-inducing agent according to (3), wherein the cancer is an MRAP2 expressing cancer.

(5) The immunity-inducing agent according to (3) or (4), wherein the cancer is leukemia, malignant lymphoma, lung cancer, brain tumor, colon cancer, melanoma, neuroblastoma, pancreatic cancer, stomach cancer, liver cancer, ovarian cancer, esophageal cancer, kidney cancer, mastocytoma or perianal adenocarcinoma.

(6) The immunity-inducing agent according to any one of (1) to (5), further comprising an immunoenhancer.

(7) The immunity-inducing agent according to (6), wherein the immunoenhancer is at least one selected from the group consisting of Freund's incomplete adjuvant, Montanide, Poly IC and derivatives thereof, CpG oligonucleotides, interleukin 12, interleukin 18, interferon α, interferon β, interferon ω, interferon γ, and Flt 3 ligand.

(8) A method for preparing an antigen-presenting cell containing a complex of the polypeptide defined in (1) and an MHC molecule, comprising contacting the polypeptide with an antigen-presenting cell from a subject ex vivo or in vitro.

(9) The method according to (8), wherein the antigen-presenting cell is a dendritic cell or B cell having an MHC class I molecule.

(10) A method for preparing a cytotoxic T cell specific to the polypeptide defined in (1), comprising contacting the antigen-presenting cell obtained by the method according to (8) or (9) with a T cell from a subject ex vivo or in vitro, thereby activating the T cell.

(11) A method for inducing immunity, comprising administering, to a subject, at least one polypeptide having immunity-inducing activity and selected from the following polypeptides (a) to (d), or a recombinant vector comprising a polynucleotide encoding the polypeptide and capable of expressing said polypeptide in vivo:

(a) a polypeptide consisting of 7 or more consecutive amino acids or a full-length sequence in the amino acid sequence represented by SEQ ID NO: 2, 4, 6, or 8 in the Sequence Listing;

(b) a polypeptide consisting of an amino acid sequence obtained by deletion, substitution or addition of one or several amino acids in the amino acid sequence represented by SEQ ID NO: 2, 4, 6, or 8 in the Sequence Listing;

(c) a polypeptide consisting of an amino acid sequence having a sequence identity of 90% or more with the amino acid sequence represented by SEQ ID NO: 2, 4, 6, or 8 in the Sequence Listing;

(d) a polypeptide comprising any of the polypeptides (a) to (c) as a partial sequence.

The present application claims the priority to JP Patent Application No. 2016-064032 filed on Mar. 28, 2016 and includes the contents described in the specification of the patent application.

Advantageous Effects of Invention

According to the present invention, there is provided a novel immunity-inducing agent useful for treatment and/or prevention for cancers, and the like. When the polypeptide used in the invention is administered to a subject, immune cells can be induced in the living body and a cancer which has already occurred can be reduced in size or regressed, as specifically shown in Examples described later. Thus, the polypeptide is useful for treating and preventing cancers.

EMBODIMENT FOR CARRYING OUT THE INVENTION

1. Polypeptide

Figure 1:
FIG. 1 This figure shows expression patterns of the identified MRAP2 gene in canine tumor tissues. Reference number 1 shows expression patterns of the canine MRAP2 gene in individual canine tumor tissues.

As a polypeptide contained as an active ingredient in the immunity-inducing agent of the present invention, polypeptides defined in the following (a) to (d) are included. Herein, the term "polypeptide" refers to a molecule formed of a plurality of amino acids which are bound via peptide linkage, and includes not only a polypeptide molecule constituted of a large number of amino acids but also a low molecular-weight molecule (i.e., an oligopeptide) constituted of a small number of amino acids, or a full-length protein.

(a) A polypeptide consisting of 7 or more consecutive amino acids or a full-length sequence in a polypeptide having the amino acid sequence represented by SEQ ID NO: 2, 4, 6, or 8 in the Sequence Listing, and having immunity-inducing activity;

(b) a polypeptide consisting of an amino acid sequence obtained by deletion, substitution or addition of one or several amino acids in the amino acid sequence represented by SEQ ID NO: 2, 4, 6, or 8 in the Sequence Listing, and having immunity-inducing activity;

(c) a polypeptide consisting of an amino acid sequence having a sequence identity of 90% or more with the amino acid sequence represented by SEQ ID NO: 2, 4, 6, or 8 in the Sequence Listing, and having immunity-inducing activity;

(d) a polypeptide comprising any of the polypeptides (a) to (c) as a partial sequence, and having immunity-inducing activity.

In the present invention, the phrase "having an(the) amino acid sequence" means that amino acid residues align in the order shown in the sequence. Accordingly, for example, the "polypeptide having the amino acid sequence represented by SEQ ID NO: 8" refers to a polypeptide having a size of 207 amino acid residues and consisting of the amino acid sequence of Met, Glu, Met, Ser, Ala . . . (omission) . . . Ile, Asp, Leu and Asp represented by SEQ ID NO: 8. The "polypeptide having the amino acid sequence represented by SEQ ID NO: 8" is sometimes simply referred to as, for example, "the polypeptide of SEQ ID NO: 8". The same is applied to the expression "having a(the) nucleotide sequence". In the phrase, the term "having" may be replaced by the term "consisting of".

Here, the term "immunity-inducing activity" refers to an ability to induce immune cells secreting cytokines such as interferon in the living body.

Whether or not the polypeptide above has an immunity-inducing activity can be confirmed by using, for example, ELISpot Assay known in the art. More specifically, the immunity-inducing activity can be evaluated by: obtaining cells like peripheral blood mononuclear cells from a living body to which the polypeptide to be evaluated for immunity-inducing activity has been administered; co-culturing the cells with the polypeptide; and measuring the amount of a cytokine produced from the cells by using a specific antibody, thereby determining the number of immune cells in the cells.

As described in Examples below, when the recombinant polypeptides of the above (a) to (d) each are administered to cancer-bearing living bodies, tumors can also be regressed due to the immunity-inducing activity of the polypeptides. Accordingly, the immunity-inducing activity can be evaluated as an ability to suppress proliferation of cancer cells or reduce the size of a cancer tissue (tumor) or eliminate a cancer tissue (tumor) (hereinafter referred to as "antitumor activity"). The antitumor activity of a polypeptide can be confirmed by actually administering the polypeptide to cancer-bearing living bodies and examining, for example, whether or not a tumor is reduced in size, for example, as specifically described in Examples below. Alternatively, the antitumor activity of a polypeptide may be evaluated by examining, for example, whether a cytotoxic T cell, which is induced by administering the polypeptide to cancer-bearing living bodies, exhibits cytotoxic activity to a tumor. The cytotoxic activity of a T cell can be determined in vivo by administering an antibody, which removes the T cell from a living body, and examining whether or not a tumor is thereby increased in size. However, the method of determining cytotoxic activity is not limited to those mentioned above.

Alternatively, the antitumor activity of the polypeptides may be evaluated by examining whether or not T cells stimulated with the polypeptides (more specifically, T cells contacted with antigen-presenting cells that present the polypeptides) exhibit cytotoxic activity against tumor cells in vitro. The T cells and the antigen-presenting cells may be contacted with each other by co-culturing both cells in a liquid medium, as described later. The cytotoxic activity may be measured by the known method called $^{51}$Cr release assay, for example, described in Int. J. Cancer, 58: p. 317, 1994. When the above-mentioned polypeptides are used for treatment and/or prevention of cancers, the immunity-inducing activity is preferably evaluated by using the antitumor activity as an indicator although such evaluation is not particularly limited thereto.

In the present invention, the amino acid sequences represented by SEQ ID NOs: 2, 4, 6, and 8, respectively, as described in the Sequence Listing are the amino acid sequences of MRAP2, which were isolated, as the polypeptides that bind to antibodies specifically present in the sera derived from cancer-bearing dogs, by the SEREX method using a cDNA library derived from canine testis and the sera of cancer-bearing dogs, and as homologs from human, cat, and mouse (see, Example 1). Human MRAP2, which is a human homolog homologous with dog MRAP2, has a nucleotide sequence identity of 91% and an amino acid sequence identity of 94%. Cat MRAP2, which is a cat homolog, has a nucleotide sequence identity of 95% and an amino acid sequence identity of 96%. Mouse MRAP2, which is a mouse homolog, has a nucleotide sequence identity of 84% and an amino acid sequence identity of 88%.

The polypeptide defined in the (a) above is a polypeptide which consists of 7 or more consecutive amino acids, preferably 8, 9 or 10 or more consecutive amino acids in the polypeptide having the amino acid sequence represented by SEQ ID NO: 2, 4, 6, or 8, and which has an immunity-inducing activity. Particularly preferably, the polypeptide has the amino acid sequence represented by SEQ ID NO: 2, 4, 6, or 8. As known in the art, if a polypeptide has approximately 7 or more amino acid residues, then the polypeptide can exhibit antigenicity and immunogenicity. As such, where the polypeptide consists of 7 or more consecutive amino acid residues or all amino acid residues (full-length sequence) in the amino acid sequence represented by SEQ ID NO: 2, 4, 6, or 8, it can possess an immunity-inducing activity and thus can be used for preparation of the immunity-inducing agent of the present invention.

As the principle of immune induction by administration of a cancer antigenic polypeptide, the following process is known: a polypeptide is incorporated into an antigen-presenting cell and then degraded into smaller fragments by peptidases in the cell, followed by presentation of the fragments on the surface of the cell. The fragments are then recognized by a cytotoxic T cell or the like, which selectively kills cells presenting the antigen. The size of the polypeptide presented on the surface of the antigen-presenting cell is relatively small and is approximately 7 to 30 amino acids. Therefore, from the viewpoint of presenting the polypeptide on the surface of the antigen-presenting cell, one preferred embodiment of the above-described polypeptide (a) is a polypeptide composed of approximately 7 to 30 consecutive amino acids in the amino acid sequence represented by SEQ ID NO: 2, 4, 6, or 8, and more preferably, a polypeptide composed of approximately 8 to 30 or approximately 9 to 30 amino acids is sufficient as the polypeptide (a). In some cases, these relatively small polypeptides are presented directly on the surface of the antigen-presenting cell without being incorporated into the antigen-presenting cells.

Further, since a polypeptide incorporated into an antigen-presenting cell is cleaved at random sites by peptidases in the cell to yield various polypeptide fragments, which are then presented on the surface of the antigen-presenting cell, administration of a large polypeptide such as the full-length region of SEQ ID NO: 2, 4, 6, or 8 inevitably causes production of polypeptide fragments by degradation in the antigen-presenting cell, which fragments are effective for immune induction via the antigen-presenting cell. Therefore, also for immune induction via antigen-presenting cells, a large polypeptide can be preferably used, and the polypeptide may be composed of not less than 30, preferably not less than 100, more preferably not less than 200 amino acids. The polypeptide may be still more preferably composed of the full-length region of SEQ ID NO: 2, 4, 6, or 8.

The polypeptide described in the (c) above is a polypeptide which is obtained by substitution, deletion and/or insertion of a small number of (preferably one or several) amino acid residues in the polypeptide described in the (a) above, which has a sequence identity of 90% or more, preferably 95% or more, more preferably 98% or more, still more preferably 99% or more, or 99.5% or more with the original sequence, and which has immunity-inducing activity. Generally, it is widely known to those skilled in the art that a protein antigen, even if it has a substitution, deletion, or insertion of a small number of amino acid residues in the amino acid sequence of the protein, may have substantially the same antigenicity as the original protein. Accordingly, a polypeptide defined in the above (c) can exhibit immunity-inducing activity, and thus, can be used in preparation of the immunity-inducing agent of the present invention. It is also preferable that the polypeptide of the above (b) is a polypeptide obtained by substitution, deletion, and/or insertion of one to several amino acid residues in the amino acid sequence represented by SEQ ID NO: 2, 4, 6, or 8. Herein, the term "several" refers to an integer of 2 to 10, preferably 2 to 6 and further preferably 2 to 4.

Here, the term "sequence identity" of amino acid sequences or nucleotide sequences means the value calculated by aligning two amino acid sequences (or nucleotide sequences) to be compared such that the number of matched amino acid residues (or nucleotides) is as the largest as possible between the amino acid sequences (or nucleotide sequences), and dividing the number of matched amino acid residues (or the number of matched nucleotides) by the total number of amino acid residues (or the total number of nucleotides), which value is represented as a percentage. When the alignment is carried out, a gap(s) is/are inserted into one or both of the two sequences to be compared as required. Such alignment of sequences can be carried out using a well-known program such as BLAST, FASTA or CLUSTAL W. When a gap(s) is/are inserted, the above-described total number of amino acid residues is the number of residues calculated by counting one gap as one amino acid residue. When the thus counted total number of amino acid residues is different between the two sequences to be compared, the sequence identity (%) is calculated by dividing the number of matched amino acid residues by the total number of amino acid residues in the longer sequence.

The 20 types of amino acids constituting naturally occurring proteins may be classified into groups in each of which similar properties are shared, for example, into neutral amino acids with side chains having low polarity (Gly, Ile, Val, Leu, Ala Met, Pro), neutral amino acids having hydrophilic side chains (Asn, Gin, Thr, Ser, Tyr, Cys) acidic amino acids (Asp, Glu), basic amino acids (Arg, Lys, His), and aromatic amino acids (Phe, Tyr, Trp). It is known that, in most cases, substitutions of amino acids within the same group do not change the properties of the polypeptide. Therefore, in cases where an amino acid residue(s) in the polypeptide (a) of the present invention is/are substituted, the probability that the immunity-inducing activity can be maintained becomes high by substitution between amino acids residues within each group, and so the substitution is preferred.

The polypeptide (d) comprises any of the polypeptides (a) to (c) as a partial sequence and has an immunity-inducing activity. That is, the polypeptide (d) has another amino acid or polypeptide added at one end or both ends of any of the polypeptides (a) to (c), and has an immunity-inducing activity. Such a polypeptide can also be used in preparation of the immunity-inducing agent of the present invention.

The above-described polypeptides can be synthesized by, for example, a chemical synthesis method such as the Fmoc method (fluorenylmethyloxycarbonyl method) or the tBoc method (t-butyloxycarbonyl method). Further, they can be synthesized by conventional methods using various types of commercially available peptide synthesizers. Further, the polypeptide of interest can be obtained using known genetic engineering techniques, by preparing a polynucleotide encoding the above polypeptide and incorporating the polynucleotide into an expression vector, which is then introduced into a host cell, followed by allowing the polypeptide to be produced in the host cell.

The polynucleotide encoding the above polypeptide can be easily prepared by a known genetic engineering technique or a conventional method using a commercially available nucleic acid synthesizer. For example, DNA having the nucleotide sequence shown in SEQ ID NO: 3 can be prepared by carrying out PCR using a canine chromosomal DNA or cDNA library as a template, and a pair of primers designed such that the nucleotide sequence shown in SEQ ID NO: 3 can be amplified using the primers. DNA having the nucleotide sequence of SEQ ID NO: 1 can be similarly prepared by using a human chromosomal DNA or cDNA library as the template. The reaction conditions for the PCR can be set appropriately, and examples thereof include, but are not limited to, repeating the reaction process of 94° C. for 30 seconds (denaturation), 55° C. for 30 seconds to 1 minute (annealing) and 72° C. for 1 minute (extension) as one cycle, for 30 cycles for example, followed by the reaction at 72° C. for 7 minutes. Further, the desired DNA can be isolated by preparing an appropriate probe(s) or primer(s) based on the information of the nucleotide sequences and the amino acid sequences shown in SEQ ID NO: 1 and 3 in Sequence Listing described herein, and screening a cDNA library of human, dog or the like using the probe(s) or primer(s). The cDNA library is preferably prepared from cells, organs or tissues expressing the protein of SEQ ID NO: 2 or 4. The above-described operations such as preparation of a probe(s) or primer(s), construction of a cDNA library, screening of a cDNA library and cloning of a gene of interest are known to those skilled in the art, and can be carried out according to the methods described in Molecular Cloning, Second Edition; Current Protocols in Molecular Biology; and/or the like. From the thus obtained DNA, DNA encoding the polypeptide (a) can be obtained. Further, since the codons encoding each amino acid are known, the nucleotide sequence of a polynucleotide encoding a specific amino acid sequence can be easily specified. Therefore, since the nucleotide sequence of a polynucleotide encoding the polypeptide (b) to (d) can also be easily specified, such a polynucleotide can also be easily synthesized using a commercially available nucleic acid synthesizer according to a conventional method.

The host cells are not restricted as long as they can express the above-described polypeptide, and examples thereof include, but are not limited to, prokaryotic cells such as *E. coli*; and eukaryotic cells such as cultured mammalian cells including monkey kidney cells COS1 and Chinese hamster ovary cells CHO; budding yeast; fission yeast; silkworm cells; and *Xenopus laevis* egg cells.

When prokaryotic cells are used as the host cells, an expression vector in which an origin that enables replication of the vector in a prokaryotic cell, promoter, ribosome binding site, DNA cloning site, terminator and/or the like is/are contained is used. Examples of the expression vector for *E. coli* include the pUC system, pBluescript II, pET expression system and pGEX expression system. By incorporating a DNA encoding the above polypeptide into such an expression vector and transforming prokaryotic host cells with the vector, followed by culturing the resulting transformants, the polypeptide encoded by the DNA can be expressed in the prokaryotic host cells. In this process, the polypeptide can also be expressed as a fusion protein with another protein.

When eukaryotic cells are used as the host cells, an expression vector for eukaryotic cells having a promoter, splicing region, poly(A) addition site and/or the like is used as the expression vector. Examples of such an expression vector include pKA1, pCDM8, pSVK3, pMSG, pSVL, pBK-CMV, pBK-RSV. EBV vector, pRS, pcDNA3.1, pSec-Tag(A, B, C), pMSG and pYES2. In the same manner as described above, by incorporating a DNA encoding the above polypeptide into such an expression vector and transforming eukaryotic host cells with the vector, followed by culturing the resulting transformants, the polypeptide encoded by the DNA can be expressed in the eukaryotic host cells. In cases where pIND/V5-His, pFLAG-CMV-2, pEGFP-N1, pEGFP-C1 or the like is used as the expression vector, the above polypeptide can be expressed as a fusion protein wherein a tag such as a His tag, FLAG tag, myc tag, HA tag or GFP, has been added.

For the introduction of the expression vector into the host cells, well-known methods such as electroporation, the calcium phosphate method, the liposome method, and the DEAE dextran method may be used.

Isolation and purification of the polypeptide of interest from the host cells can be carried out by a combination of known separation operations. Examples of the known separation operations include, but are not limited to, treatment with a denaturant such as urea or with a surfactant; sonication treatment; enzyme digestion; salting-out or solvent fractional precipitation; dialysis; centrifugation; ultrafiltration; gel filtration; SDS-PAGE; isoelectric focusing; ion-exchange chromatography; hydrophobic chromatography; affinity chromatography; and reversed-phase chromatography.

The polypeptides obtained by the above method also include, as mentioned above, those being in the form of a fusion protein with another arbitrary protein. Examples thereof include fusion proteins with glutathione S-transferase (GST) or with a His tag. Such a polypeptide that is in the form of a fusion protein also falls within the scope of the present invention as the above polypeptide (d). Further, in some cases, a polypeptide expressed in a transformed cell is modified in various ways in the cell after translation. Such a post-translationally modified polypeptide also falls within the scope of the present invention as long as it has an immunity-inducing activity. Examples of such a post-translational modification include: elimination of N-terminal methionine; N-terminal acetylation; glycosylation; limited degradation by an intracellular protease; myristoylation; isoprenylation; and phosphorylation.

2. Immunity-Inducing Agent

As described more specifically in Examples described later, a tumor can be regressed by administration of the polypeptide having an immunity-inducing activity to a tumor-bearing living body. Thus, the immunity-inducing agent of the present invention can be used as therapeutic and/or preventive agent for cancers. Further, the polypeptide having an immunity-inducing activity be used in a method of treating and/or preventing cancers by immunity induction.

Here, the terms "tumor" and "cancer" mean a malignant neoplasm, and are used interchangeably.

In this case, the target cancer, which is not particularly limited, is any cancer that expresses MRAP2, preferably, a cancer that significantly more highly expresses MRAP2 than normal cells, specifically, leukemia, malignant lymphoma, lung cancer, brain tumor, colon cancer, melanoma, neuroblastoma, pancreatic cancer, stomach cancer, liver cancer, ovarian cancer, esophageal cancer, kidney cancer, mastocytoma or perianal adenocarcinoma. Examples of these specific cancers include, but are not limited to, acute non-lymphocytic leukemia, chronic lymphocytic leukemia, acute granulocytic leukemia, chronic granulocytic leukemia, acute promyelocytic leukemia, adult T-cell leukemia, aleukemic leukemia, leukocythemic leukemia, basophilic leukemia, blastic leukemia, bovine leukemia, chronic myeloleukemia, leukemia cutis, embryonal leukemia, eosinophilic leukemia, Gross leukemia, Rieder cell leukemia, Schilling's leukemia, stem cell leukemia, subleukemic leukemia, undifferentiated cell leukemia, hairy cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphotropic leukemia, lymphoid leukemia, lymphosarcoma cell leukemia, mast cell leukemia, megakaryocytic leukemia, micromyeloblastic leukemia, monocytic leukemia, myeloblastic leukemia, myeloleukemia, myeloid granulocytic leukemia, myelomonocytic leukemia, Naegeli leukemia, plasma cell leukemia, plasmacytic leukemia, promyelocytic leukemia, non-Hodgkin lymphoma [Burkitt lymphoma (BL), small lymphocytic lymphoma/chronic lymphocytic leukemia (SLL/CLL), mantle cell lymphoma (MCL), follicular lymphoma (FL), diffuse large B-cell lymphoma (DLCL), marginal zone lymphoma (MZL), hairy cell leukemia (HCL), lymphoplasmacytic leukemia (LPL), extranodal marginal zone lymphoma of mucosa-associated lymphoid tissue (MALT), mediastinal large cell lymphoma, intravascular large cell lymphoma, primary effusion lymphoma, precursor B-cell lymphoblastic leukemia/lymphoma, precursor T-cell and NK-cell lymphoma (precursor T-cell lymphoblastic lymphoma, NK-cell lymphoblastic lymphoma), mature T- and NK-cell neoplasms (including peripheral T-cell lymphoma and leukemia (PTL)], adult T-cell leukemia/T-cell lymphoma and large granular lymphocytic leukemia, chronic T-cell lymphocytic leukemia/prolymphocytic leukemia, T-cell large granular lymphocytic leukemia, aggressive NK-cell leukemia, extranodal T-/NK-cell lymphoma, enteropathy-type T-cell lymphoma, hepatosplenic T-cell lymphoma, anaplastic large cell lymphoma (ALCL), angiocentric and angioimmunoblastic T-cell lymphoma, mycosis fungoides/Sezary's syndrome, cutaneous T-cell lymphoma (CTCL), Hodgkin lymphoma, non-small cell lung cancer, squamous cell carcinoma (epidermoid cancer), lung adenocarcinoma, large cell lung cancer, small cell lung cancer, glioma, astrocytoma, brainstem glioma, ependymoma, oligodendroglioma, nonglial tumor, acoustic neurilemoma, craniopharyngioma, medulloblastoma, meningioma, pineocytoma, pineoblastoma, primary brain lymphoma, germ cell tumor, superficial colon cancer, protuberant colon cancer, ulcerative infiltrative colon cancer, diffuse infiltrative colon cancer, basal cell cancer, prickle cell cancer, melanoma, superficial spreading melanoma, nodular melanoma, malignant lentigo melanoma, acral lentiginous melanoma, neuroblastoma, ganglioneuroblastoma, ganglioma, insulinoma, gastrinoma, glucagonoma, VIPoma, somatostatin-secreting tumor, carcinoid, islet cell tumor, protuberant stomach cancer, ulcerative localized stomach cancer, ulcerative infiltrative stomach cancer, diffuse infiltrative stomach cancer, hepatocellular cancer and hepatoblastoma, epithelial ovarian cancer, borderline tumor, germ cell tumor, stromal tumor, serous adenocarcinoma, clear cell adenocarcinoma, endometrioid adenocarcinoma, transitional cell cancer, mucous adenocarcinoma, mixed ovarian cancer, squamous cell carcinoma, esophageal adenocarcinoma, renal cell cancer, kidney adenocarcinoma, hypernephroma, renal fibrosarcoma, transitional cell cancer (renal pelvis and/or uterer), mastocytoma, perianal adenoma, and perianal adenocarcinoma.

The subject of interest (i.e., the animal) is preferably a mammal; more preferably a mammal comprising primate, pet animal, any animal raised in zoo or the like, farm animal, and racing animal; and particularly preferably human, dog, or cat.

The administration route of the immunity-inducing agent of the present invention to a living body may be either oral administration or parenteral administration, and is preferably parenteral administration such as intramuscular administration, subcutaneous administration, intravenous administration or intraarterial administration. When the immunity-inducing agent is used for treatment of cancers, it may be administered to a regional lymph node in the vicinity of the tumor to be treated, in order to enhance its anticancer activity. The dose may be any dose as long as the dose is effective for immunity induction, and, for example, in cases where the agent is used in treatment and/or prevention of cancers, the dose may be one effective for treatment and/or prevention of the cancers. The dose effective for treatment and/or prevention of cancers is appropriately selected depending on the size and symptoms of a tumor and the like, and the effective dose is usually 0.0001 μg to 1000 μg, preferably 0.001 μg to 1000 μg per subject animal per day, which may be administered once or in several times. The agent is preferably administered in several times, every several days to several months. As specifically indicated in the Examples below, the immunity-inducing agent of the present invention can cause regression of a tumor. Therefore, since the agent can exert its anticancer activity also against a small number of cancer cells at an early stage, development or recurrence of cancer can be prevented by using the agent before development of the cancer or after treatment of the cancer. Thus, the immunity-inducing agent of the present invention is effective for both treatment and prevention of cancers.

The immunity-inducing agent of the present invention may consist of the polypeptide(s) alone or may be in the form of a preparation obtained by appropriately admixing additives such as pharmacologically acceptable carrier, diluent, excipient, and the like, which are suitable for dosage forms. A method for making a preparation, as well as usable additives, is well known in the field of pharmaceutical preparations, and any methods and additives can be used. Examples of the additives include, are not limited to, diluents such as physiological buffer solutions; excipients such as sugar, lactose, cornstarch, calcium phosphate, sorbitol and glycine; binders such as syrup, gelatin, gum Arabic, sorbitol, polyvinyl chloride and tragacanth; and lubricants such as magnesium stearate, polyethylene glycol, talc and silica. Examples of dosage forms may include oral preparations such as tablets, capsules, granules, powder and syrups; and parenteral preparations such as inhalants, injections, suppositories and solutions. These preparations can be produced by methods generally known in the art.

The immunity-inducing agent of the present invention may be used in combination with an immunoenhancer capable of enhancing the immune response in a living body. The immunoenhancer may be contained in the immunity-inducing agent of the present invention or administered as a separate composition to a patient in combination with the immunity-inducing agent of the present invention.

Examples of the immunoenhancer include adjuvants. Adjuvants can enhance the immune response by providing a reservoir of antigen (extracellularly or within macrophages), activating macrophages and stimulating specific sets of lymphocytes, thereby enhancing the immune response and thus the anticancer action. Therefore, especially in cases where the immunity-inducing agent of the present invention is used for treatment and/or prevention of cancers, the immunity-inducing agent preferably comprises an adjuvant, in addition to the above-described polypeptide that is an effective ingredient. Many types of adjuvants are well-known in the art, and any of these adjuvants may be used.

Specific examples of the adjuvants include MPL (SmithKline Beecham), homologues of *Salmonella minnesota* Re 595 lipopolysaccharide obtained after purification and acid hydrolysis of the lipopolysaccharide; QS21 (SmithKline Beecham), pure QA-21 saponin purified from an extract of *Quillja saponaria*; DQS21 described in WO96/33739 (SmithKline Beecham); QS-7, QS-17, QS-18 and QS-L1 (So and 10 others, "Molecules and Cells", 1997, Vol. 7, p. 178-186); Freund's incomplete adjuvant; Freund's complete adjuvant; vitamin E; Montanide; Alum; CpG oligonucleotides (see, for example, Kreig and 7 others, Nature, Vol, 374, p. 546-549); poly-IC and derivatives thereof (e.g., poly ICLC); and various water-in-oil emulsions prepared from biodegradable oils such as squalene and/or tocopherol. Among them, the preferred are Freund's incomplete adjuvant, Montanide, poly-IC and derivatives thereof, and CpG oligonucleotides. The mixing ratio between the above-described adjuvant and the polypeptide is typically approximately 1:10 to 10:1, preferably approximately 1:5 to 5:1, more preferably approximately 1:1. However, the adjuvant is not limited to the above-described examples, and adjuvants known in the art other than those described above may also be used when the immunity-inducing agent of the present invention is administered (see, for example, Goding, "Monoclonal Antibodies: Principles and Practice, 2nd edition", 1986). Preparation methods for mixtures or emulsions of a polypeptide and an adjuvant are well-known to those skilled in the art of vaccination.

Further, in addition to the above-described adjuvants, factors that stimulate the immune response of interest may be used as the above-described immunoenhancer. For example, various cytokines having a property to stimulate lymphocytes and/or antigen-presenting cells may be used as the immunoenhancer in combination with the immunity-inducing agent of the present invention. A number of such cytokines capable of enhancing the immune response are known to those skilled in the art, and examples thereof include, but are not limited to, interleukin-12 (IL-12), GM-CSF, IL-18, interferon-α, interferon-β, interferon-ω, interferon-γ, and Flt3 ligand, which have been reported to enhance the prophylactic action of vaccines. Such factors may be used as the immunoenhancer and administered to a patient by adding it to the immunity-inducing agent of the present invention or administered as an independent composition in combination with the immunity-inducing agent of the present invention.

3. Antigen-Presenting Cells or Cytotoxic T Cells

By bringing the above-described polypeptide into contact with antigen-presenting cells (from a subject) ex vivo or in vitro, the antigen-presenting cells can be made to present the polypeptide. That is, the polypeptides (a) to (d) described above can be used as the agent for treating antigen-presenting cells. Examples of the antigen-presenting cells which may be preferably used include dendritic cells or B cells having an MHC class I molecule. Various MHC class I molecules have been identified and are well-known. MHC molecules in human are called HLA. Examples of HLA class I molecules include HLA-A, HLA-B and HLA-C, more specifically, HLA-A1, HLA-A0201, HLA-A0204, HLA-A0205, HLA-A0206, HLA-A0207, HLA-A11, HLA-A24, HLA-A31 HLA-A6801, HLA-B7, HLA-B8, HLA-B2705, HLA-B37, HLA-Cw0401 and HLA-Cw0602, The dendritic cells or B cells having an MHC class I molecule can be prepared from peripheral blood by a well-known method. For example, tumor-specific dendritic cells can be induced by inducing dendritic cells from bone marrow, umbilical cord blood or patient's peripheral blood using granulocyte-macrophage colony-stimulating factor (GM-CSF) and IL-3 (or IL-4), and then adding a tumor-associated peptide to the culture system.

By administering an effective amount of such dendritic cells, a response desired for therapy of a cancer can be induced. As the cells to be used, bone marrow or umbilical cord blood donated by a healthy individual, or bone marrow, peripheral blood or the like from the patient himself may be used. When autologous cells of the patient are used, high safety can be attained and serious side effects are expected to be avoided. The peripheral blood or bone marrow may be any of fresh sample, cold-stored sample and frozen sample.

As for the peripheral blood, whole blood may be cultured or the leukocyte components alone may be separated and cultured, and the latter is more efficient and thus preferred. Further, among the leukocyte components, mononuclear cells may be separated. In cases where the cells are originated from bone marrow or umbilical cord blood, the whole cells constituting the bone marrow may be cultured, or mononuclear cells may be separated therefrom and cultured. Peripheral blood, the leukocyte components thereof and bone marrow cells contain mononuclear cells, hematopoietic stem cells and immature dendritic cells, from which dendritic cells are originated, and also CD4-positive cells and the like. As for the cytokine to be used, the production method thereof is not restricted, and a naturally-occurring or recombinant cytokine or the like may be employed as long as its safety and physiological activity have been confirmed. Preferably, a preparation with assured quality for medical use is used in a minimum necessary amount. The concentration of the cytokine(s) to be added is not restricted as long as the dendritic cells are induced at the concentration, and usually, the total concentration of the cytokine(s) is preferably approximately 10-1000 ng/mL more preferably approximately 20-500 ng/mL. The cultivation may be carried out using a well-known medium usually used for cultivation of leukocytes. The culturing temperature is not restricted as long as proliferation of the leukocytes is attained at the temperature, and a temperature of about 37° C., which is the body temperature of human, is most preferred. The atmospheric environment during the culturing is not restricted as long as proliferation of the leukocytes is attained under the environment, and 5% $CO_2$ is preferably ventilated. The culturing period is not restricted as long as a necessary number of the cells are induced during such period, being usually 3 days to 2 weeks. As for the apparatuses used for separation and cultivation of the cells, appropriate apparatuses, preferably those whose safety upon application to medical uses have been confirmed and whose operations are stable and simple, may be employed. In particular, as for the cell-culturing apparatus, not only a general vessel such as Petri dish, flask or bottle, but also a layer type vessel, multistage vessel, roller bottle, spinner type bottle, bag type culturing vessel, hollow fiber column or the like may be used.

The method itself of contacting the polypeptide as mentioned above with an antigen-presenting cell ex vivo or in vitro, can be carried out by a method well known in the art, for example, by culturing the antigen-presenting cell in a culture liquid containing the polypeptide. The concentration of the peptide in the medium, which is not particularly limited, is usually approximately 1 to 100 μg/ml and preferably approximately 5 to 20 μg/ml. The cell density during culturing, which is not particularly limited, is usually approximately $10^3$ to $10^7$ cells/ml and preferably approximately $5 \times 10^4$ to $5 \times 10^6$ cells/ml. The culture is preferably carried out by routine methods at 37° C. in 5% $CO_2$ atmosphere. The length of a peptide that can be presented by the antigen-presenting cell on the surface thereof is usually approximately 30 amino acid residues at a maximum. Accordingly, when the antigen-presenting cell is contacted with the polypeptide ex vivo or in vitro, the polypeptide may be prepared so as to have a length of approximately 30 amino acid residues or less; however, the length is not limited to this.

By culturing the antigen-presenting cell in the presence of the above polypeptide, the peptide is integrated into an MHC molecule of the antigen-presenting cell and presented on the surface of the antigen-presenting cell. Accordingly, it is possible to prepare an isolated antigen-presenting cell containing a complex of the polypeptide and the MHC molecule.

Accordingly, the present invention further provides a method for preparing an antigen-presenting cell containing a complex of the polypeptide as mentioned above and an MHC molecule, comprising contacting the polypeptide with an antigen-presenting cell from a subject ex vivo or in vitro.

The present invention also provides an antigen-presenting cell characterized by containing a complex of the polypeptide as mentioned above and an MHC molecule and obtained by the method.

By contacting an antigen-presenting cell, which is prepared in the above-mentioned manner and contains a complex of the polypeptide as mentioned above and an MHC molecule, with a T cell ex vivo or in vitro, the cytotoxic T cell specific to the polypeptide can be induced and proliferated. The contact can be made by co-culturing the antigen-presenting cell and the T cell in a liquid medium; for example, by suspending the antigen-presenting cell in a liquid medium, placing the resultant suspension in a container such as wells of a micro plate, adding the T cell to the wells, and culturing them. The mixing ratio of the antigen-presenting cell and the T cell during the co-culture, which is not particularly limited, is usually, approximately 1:1 to 1:100, preferably approximately 1:5 to 1:20 in terms of a ratio of the numbers of the cells. The density of the antigen-presenting cell in the liquid medium, which is not particularly limited, is usually, approximately 100 to 10,000,000 cells/ml and preferably approximately 10,000 to 1,000,000 cells/ml. The co-culture is preferably carried out by routine methods at 37° C. in 5% $CO_2$ atmosphere. The culture time, which is not particularly limited, is usually, 2 days to 3 weeks and preferably about 4 days to 2 weeks. The co-culture is preferably carried out in the presence of one or more types of interleukins such as IL-2, IL-6, IL-7 and IL-12. In this case, the concentrations of IL-2 and IL-7 are usually approximately 5 to 20 U/ml, the concentration of IL-6 is usually approximately 500 to 2000 U/ml, and the concentration of IL-12 is usually approximately 5 to 20 ng/ml; however, the concentrations are not limited to these. The co-culture may be repeated once or several times by supplementing the fresh antigen-presenting cell. For example, an operation, which comprises discarding the culture supernatant after co-culture, adding a suspension of the fresh antigen-presenting cell, and carrying out co-culture, may be repeated once or several times. The co-culturing conditions may be the same as above.

Through the co-culture, the cytotoxic T cell specific to the polypeptide is induced and proliferated. Accordingly, the above-mentioned polypeptide can use to prepare isolated T cells that selectively bind a complex of the polypeptide and the MHC molecule.

Accordingly, the present invention further provides a method for preparing a cytotoxic T cell specific to the polypeptide as mentioned above, comprising contacting the antigen-presenting cell with a T cell from a subject ex vivo or in vitro to activate the T cell.

The present invention also provides a cytotoxic T cell specific to the polypeptide as mentioned above, obtained by this method.

As described in Examples below, the MRAP2 gene is specifically expressed in leukemia, malignant lymphoma, lung cancer, brain tumor, colon cancer, melanoma, neuroblastoma, pancreatic cancer, stomach cancer, liver cancer, ovarian cancer, esophageal cancer, kidney cancer, mastocytoma or perianal adenocarcinoma. Accordingly, in these cancers, it is thought that MRAP2 is significantly more largely present than in normal cells. If the cytotoxic T cell prepared in the above-described manner is administered in vivo and a part of the MRAP2 polypeptide existing in cancer cells is presented by the MHC molecule on the surface of a cancer cell, the cytotoxic T cell can damage the cancer cell by using the part of the MRAP2 polypeptide as a marker. The antigen-presenting cell presenting a part of the MRAP2 polypeptide can induce and proliferate the cytotoxic T cell specific to the polypeptide in vivo. Thus, cancer cells can also be damaged by administering the antigen-presenting cell to a living body. More specifically, the cytotoxic T cell and the antigen-presenting cell prepared by use of the above-mentioned polypeptide are also useful for treating and/or preventing cancer similarly to the immunity-inducing agent of the present invention.

In cases where the above-described isolated antigen-presenting cells or isolated T cells are administered to a subject, these are preferably prepared by treating antigen presenting cells or T cells collected from the patient to be treated with the polypeptide (a) to (d) as described above in order to avoid the immune response in the living body that attacks these cells as foreign bodies.

The treating and/or preventing agent for cancer comprising, as an effective ingredient, isolated antigen-presenting cells or T cells is preferably administered via a parenteral administration route, for example, by intravenous or intraarterial administration. The dose is appropriately selected depending on the symptoms, the purpose of administration and the like, and is usually 1 cell to 10,000,000,000,000 cells, preferably 1,000,000 cells to 1,000,000,000 cells, which dose is preferably administered once every several days to once every several months. The preparation may be, for example, the cells suspended in physiological buffered saline, and the preparation may be used in combination with other anticancer agent(s), cytokine(s) or the like. Further, one or more additives well-known in the field of pharmaceuticals may also be added.

4. DNA Vaccine

Also by expressing a polynucleotide encoding any of the polypeptides (a) to (d) in the body of a subject animal, antibody production and cytotoxic T cells can be induced in the living body, and an effect comparable to that obtained in the case of administration of the polypeptide can be obtained. That is, the immunity-inducing agent of the present invention may be one comprising, as an active ingredient, a recombinant vector comprising a polynucleotide encoding any of the polypeptides (a) to (d), wherein the recombinant vector is capable of expressing the polypeptide in a living body. Such a recombinant vector capable of expressing an antigenic polypeptide as shown in Examples described below is also called a DNA vaccine.

The vector used for production of the DNA vaccine is not restricted as long as it is a vector capable of expressing the polypeptide in a cell of a subject animal (preferably in a mammalian cell), and may be either a plasmid vector or a virus vector, and any vector known in the field of DNA vaccines may be used. The polynucleotide such as DNA or RNA encoding the above-described polypeptide can be easily prepared as mentioned above by a conventional method. Incorporation of the polynucleotide into the vector can be carried out using a method well-known to those skilled in the art.

The administration route of the DNA vaccine is preferably a parenteral route such as intramuscular, subcutaneous, intravenous or intraarterial administration, and the dose may be appropriately selected depending on the type of the antigen and the like, and is usually approximately 0.1 μg to 100 mg, preferably approximately 1 μg to 10 mg in terms of the weight of the DNA vaccine per 1 kg of body weight.

Examples of the method using a virus vector include methods in which a polynucleotide encoding the above-described polypeptide is incorporated into an RNA virus or DNA virus, such as a retrovirus, adenovirus, adeno-associated virus, herpes virus, vaccinia virus, pox virus, poliovirus or Sindbis virus, and then a subject animal is infected with the resulting virus. Among these methods, those using a retrovirus, adenovirus, adeno-associated virus, vaccinia virus or the like are especially preferred.

Examples of other methods include a method wherein an expression plasmid is directly intramuscularly administered (DNA vaccine method), a liposome method, a lipofectin method, a microinjection method, a calcium phosphate method and an electroporation method, and the DNA vaccine method and the liposome method are especially preferred.

Methods for actually allowing a gene encoding the above-described polypeptide used in the present invention to act as a drug include an in vivo method wherein the gene is directly introduced into the body, and an ex vivo method wherein a certain kind of cells are collected from a subject animal and the gene is introduced into the cells outside the body, followed by returning the cells to the body (Nikkei Science, 1994, April, p. 20-45; The Pharmaceutical Monthly, 1994, Vol. 36, No. 1, p. 23-48; Experimental Medicine, Extra Edition, 1994, Vol. 12, No. 15; and references cited in these literatures, and the like). The in vivo method is more preferred.

When the gene is administered by the in vivo method, it may be administered through an appropriate administration route depending on a disease to be treated, symptom and so on. The gene may be administered by, for example, intravenous, intraarterial, subcutaneous or intramuscular administration. When the gene is administered by the in vivo method, it may be formulated into a preparation such as a solution, and in general, it is formulated into an injection solution or the like containing DNA encoding the above-described polypeptide of the present invention as an active ingredient, and where needed, a routine carrier may be further added to the solution. In the case of a liposome or membrane fusion liposome (e.g., Sendai virus (HVJ)-liposome) containing the DNA, the liposome may be formulated into a liposome preparation such as a suspension, a frozen preparation, or a centrifugally concentrated frozen preparation.

In the present invention, for example, "the nucleotide sequence represented by SEQ ID NO:1" includes not only the nucleotide sequence represented by SEQ ID NO:1 itself, but also the sequence complementary thereto. Thus, for example, "the polynucleotide having the nucleotide sequence represented by SEQ ID NO:1" includes a single-stranded polynucleotide having the nucleotide sequence represented by SEQ ID NO:1 itself, a single-stranded polynucleotide having the nucleotide sequence complementary thereto, and a double-stranded polynucleotide composed of these single-stranded polynucleotides. When a polynucleotide encoding a polypeptide used in the present invention is prepared, any one of these nucleotide sequences is appropriately selected, and those skilled in the art can easily carry out the selection.

EXAMPLES

Now, the present invention will be more specifically described below based on Examples.

Example 1

Obtaining Novel Cancer Antigen Protein by SEREX Method (1) Preparation of cDNA Library Total RNA was extracted from canine testes in accordance with the Acid-guanidium-Phenol-Chloroform method, and then, poly(A) RNA was purified by using Oligotex-dT30 mRNA purification Kit (Takara Shuzo Co., Ltd.) in accordance with the protocol attached to the kit.

Using the obtained mRNA (5 µg), a cDNA phage library was synthesized. For the preparation of the cDNA phage library, cDNA Synthesis kit, Zap-cDNA Synthesis Kit or ZAP-cDNA GigapackIII Gold Cloning Kit (STRATA-GENE) was used in accordance with the protocol attached to the kit. The size of the prepared cDNA phage library was $1\times10^6$ pfU/ml.

(2) Screening of cDNA Library with Serum

Using the prepared cDNA phage library, immunoscreening was carried out. More specifically, host E. coli (XL1-Blue MRF') was infected with the phage so as to obtain approximately 2500 clones in an NZY agarose plate of φ90×15 mm and cultured at 42° C. for 3-4 hours to obtain plaques. The plate was covered with nitrocellulose membrane (Hybond C Extra: GE Healthcare Bio-Science) impregnated with IPTG (isopropyl-β-D-thiogalactoside) at 37° C. for 4 hours to induce protein expression and the protein was transferred to the membrane. Thereafter, the membrane was taken, soaked in TBS (10 mM Tris-HCl, 150 mM NaCl pH7.5) containing 0.5% of skim milk powder, and shaken at 4° C. overnight to suppress a nonspecific reaction. This filter was allowed to react with the 500-fold diluted serum of a canine patient at room temperature for 2 to 3 hours.

As the sera of canine patients mentioned above, the sera taken from leukemia dogs were used. The sera were stored at −80° C. and pretreated immediately before use. The method of the pretreatment of the sera was as follows. That is, first, the host *Escherichia coli* (XL1-Blure MRF') was infected with λ ZAP Express phage into which no foreign gene was inserted, and then cultured on a NZY plate medium at 37° C. overnight. Subsequently, 0.2 M NaHCO$_3$ buffer (pH8.3) containing 0.5 M NaCl was added to the plate, and the plate was left to stand at 4° C. for 15 hours, followed by collecting the supernatant as an *Escherichia coli*/phage extract. Thereafter, the collected *Escherichia coli*/phage extract was allowed to flow through a NHS-column (GE Healthcare Bio-Science) to immobilize proteins derived from *Escherichia coli*/phage onto the column. The serum from the canine patient was allowed to flow through and to react with the protein-immobilized column to remove antibodies adsorbed to *Escherichia coli* and phage from the serum. The serum fraction passed though the column was diluted 500 fold with TBS containing 0.5% of skim milk powder, and the resulting diluent was used as a material for immunoscreening.

The above membrane on which the thus treated serum and the proteins were blotted was washed 4 times with TBS-T (0.05% Tween 20/TBS), and allowed to react with goat anti-dog IgG (Goat anti Dog IgG–h+L HRP conjugated; BETHYL Laboratories) 5,000-fold diluted with TBS containing 0.5% skim milk powder as a secondary antibody at room temperature for 1 hour, followed by detection by the enzyme coloring reaction using the NBT/BCIP reaction solution (Roche). Colonies at positions where a positive coloring reaction was observed were recovered from the NZY agarose plate having a size of Φ90×15 mm, and dissolved in 500 µl of SM buffer (100 mM NaCl, 10 mM MgClSO$_4$, 50 mM Tris-HCl, 0.01% gelatin; pH 7.5). The screening was repeated as a second and third screening in the same manner as described above until a single coloring reaction-positive colony was obtained, thereby isolating one positive clone after screening of approximately 10,000 phage clones reactive with IgG in the serum.

(3) Sequence-Identity Search of Isolated Antigen Gene

In order to subject the single positive clone isolated by the above-described method to nucleotide sequence analysis, an operation for conversion of the phage vector to a plasmid vector was carried out. Specifically, a solution (200 µL) containing host *Escherichia coli* (XL1-Blue MRF) prepared so as to show an absorbance OD$_{600}$ of 1.0, a purified phage solution (100 µL), and further 1 µL of ExAssist helper phage (STRATAGENE) were mixed and allowed to react at 37° C. for 15 minutes. LB medium (3 mL) was added and cultivation was carried out at 37° C. for 2.5-3 hours. The resulting culture was immediately kept in a water bath at 70° C. for 20 minutes, and then was centrifuged at 4° C. at 1000×g for 15 minutes to collect the supernatant as a phargemid solution. Subsequently, a solution (200 µL) containing a phargemid host *Escherichia coli* (SOLR) prepared so as to have an absorbance OD$_{600}$ of 1.0 and the purified phage solution (10 µL) were mixed and allowed to react at 37° C. for 15 minutes. The resultant solution (50 µL) was seeded on an ampicillin (final concentration: 50 mg/mL)-containing LB agar medium and cultured at 37° C. overnight. A single transformed SOLR colony was picked up, cultured in ampicillin (final concentration: 50 µg/mL)-containing LB medium at 37° C. and, thereafter, purified by QIAGEN plasmid Miniprep Kit (QIAGEN) to obtain a plasmid DNA having a desired insert.

The purified plasmid was subjected to the primer walking using T3 primer represented by SEQ ID NO: 9 and T7 primer represented by SEQ ID NO: 10 to analyze the full-length sequence of the insert. The gene sequence represented by SEQ ID NO: 3 was obtained by the sequencing analysis. Using the nucleotide sequence of the gene and amino acid sequence therefor, the sequence identity search, which is a search for sequence identity with known genes, was carried out by the sequence identity search program BLAST search (http://www.ncbi.nlm.nih.gov/BLAST/). As a result, it was found that the gene obtained above is MRAP2 gene. In the human MRAP2, which is a human homolog of canine MRAP2, the nucleotide-sequence identity was 91% and the amino acid sequence identity was 94%. In cat homolog, i.e., cat MRAP2, the nucleotide sequence identity was 95% and the amino acid sequence identity was 96%. In mouse homolog, i.e., mouse MRAP2, the nucleotide sequence identity was 84% and the amino acid sequence identity was 88%. The nucleotide sequences of the human MRAP2 is represented by SEQ ID NO: 1 and the amino acid sequences thereof are represented by SEQ ID NO: 2. The nucleotide sequence of the cat MRAP2 is represented by SEQ ID NO: 5 and the amino acid sequence therefor is represented by SEQ ID NO: 6. The nucleotide sequence of the mouse MRAP2 is represented by SEQ ID NO: 7 and the amino acid sequence thereof is represented by SEQ ID NO: 8.

(4) Gene Expression Analysis in Different Tissues

Figure 2:
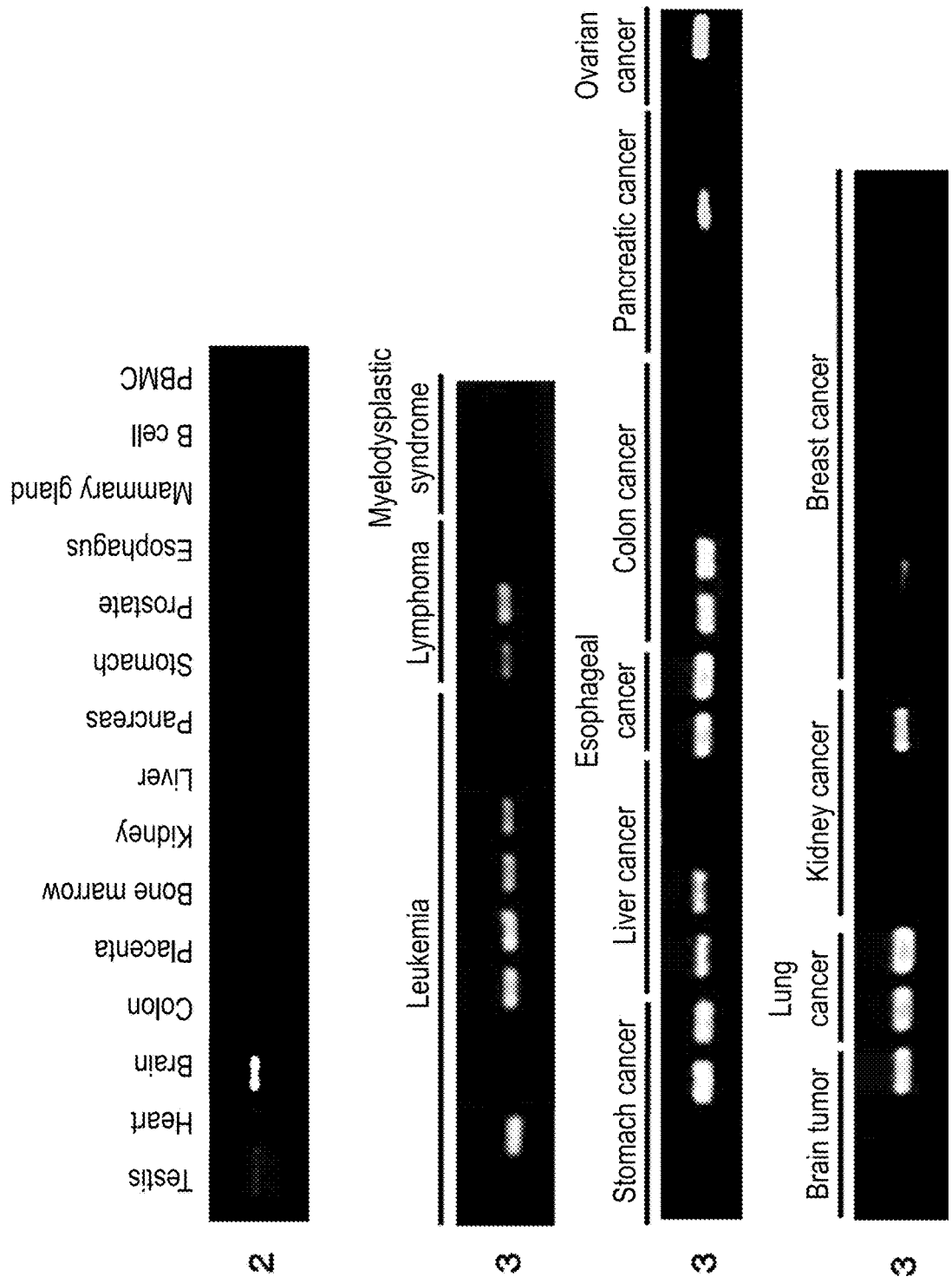
FIG. 2 This figure shows expression patterns of the identified MRAP2 gene in individual human tissues and cancer cell lines. Reference number 2 shows expression patterns of the human MRAP2 gene in individual human normal tissues; and reference number 3 shows expression patterns of the human MRAP2 gene in individual human cancer cell lines. In the figure, PBMC represents peripheral blood mononuclear cells.
Figure 3:
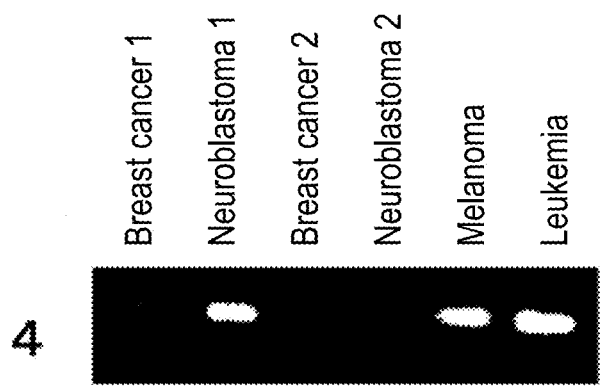
FIG. 3 This figure shows expression patterns of the identified MRAP2 gene in individual mouse cancer cell lines. Reference number 4 shows expression patterns of the mouse MRAP2 gene in individual mouse cancer cell lines.

Expression of the genes obtained by the above method in normal tissues and tumor tissues and cancer cell lines from dogs, humans and mice was examined by a RT-PCR (Reverse Transcription-PCR) method. The reverse transcription reaction was carried out as follows. First, total RNAs were extracted from individual tissues (50-100 mg) and individual cell lines ($5$-$10 \times 10^6$ cells) by use of TRIZOL reagent (Life Technology) in accordance with the protocol attached. Using the total RNAs, cDNAs were synthesized by using Superscript First-Strand Synthesis System for RT-PCR (Life Technology) in accordance with the protocol attached. As the cDNAs of the human normal tissues (from the brain, testis, colon, and placenta), gene pool cDNA (Life Technology), QUICK-Clone cDNA (Clontech) and Large-Insert cDNA Library (Clontech) were used. The PCR reaction was carried out by using the gene specific primers obtained (canine primers are represented by SEQ ID NOs: 11 and 12, human primers are represented by SEQ ID NOs: 13 and 14, mouse primers are represented by SEQ ID NOs: 15 and 16), as follows. That is, reagents were added to the attached buffer wherein the reagents contain 0.25 µL of the sample prepared by the reverse transcription reaction, the above primers (2 µM for each), dNTPs (0.2 mM for each) and a 0.65 U ExTaq polymerase (Takara Shuzo Co., Ltd.). The reaction mixture 25 µL in total was subjected to PCR using a Thermal Cycler (BIO RAD). In the PCR, 30 cycles were repeated wherein one cycle consists of the treatments: at 94° C. for 30 seconds; 55° C. for 30 seconds; and at 72° C. for one minute. As a result, as shown in FIG. 1, the canine MRAP2 gene was strongly expressed in canine tumor tissues, i.e., mastocytoma and perianal adenocarcinoma tissues (FIG. 1). The human MRAP2 gene was not expressed in almost all normal human tissues, but it was strongly expressed in human cancer cells, i.e., leukemia, malignant lymphoma, lung cancer, brain tumor, colon cancer, pancreatic cancer, stomach cancer, liver cancer, ovarian cancer, esophageal cancer, and kidney cancer cell lines (FIG. 2). Furthermore, the expression of the mouse MRAP2 gene was detected in leukemia, melanoma, and neuroblastoma cell lines (FIG. 3).

Example 2

Analysis of Cancer Antigenicity of MRAP2 In Vivo (1) Preparation of Recombinant Vector Expressing Mouse MRAP2 In Vivo A recombinant vector expressing mouse MRAP2 in vivo was prepared based on the nucleotide sequence represented by SEQ ID NO: 7 in accordance with the following method. PCR was carried out as follows. A reaction mixture was prepared by adding reagents: cDNAs (1 µL), which were prepared from mouse leukemia cell line EL4 (purchased from ATCC) whose expression was observed in Example 1, two types of primers (0.4 µM for each) having EcoRI and NotI restriction enzyme cleaved sequences (represented by SEQ ID NOs: 17 and 18), 0.2 mM dNTPs, and 1.25 U PrimeSTAR HS polymerase (Takara Shuzo Co., Ltd.), and the attached buffer so as to obtain a total amount of 50 µL; and subjected to PCR using a Thermal Cycler (BIO RAD). In the PCR, 30 cycles were repeated wherein one cycle consists of the treatments: at 98° C. for 10 seconds; at 55° C. for 15 seconds; and at 72° C. for 1 minute. The above-mentioned two types of primers were used for amplifying a region encoding a full-length amino acid sequence represented by SEQ ID NO: 8. After the PCR, the amplified DNA was electrophoresed on 1% agarose gel, and a DNA fragment of approximately 600 bp was purified by use of QIAquick Gel Extraction Kit (QIAGEN).

The purified DNA fragment was ligated to the cloning vector pCR-Blunt (Life Technology), which vector was then transformed into *E. coli* cells, followed by collecting the plasmid vector. By its sequencing, it was confirmed that the sequence of the amplified gene fragment was identical with a desired sequence. The plasmid whose sequence was identical with the desired sequence was treated with EcoRI and NotI restriction enzymes. After purification was carried out with QIAquick Gel Extraction Kit, the desired gene sequence was inserted into the mammalian expression vector pcDNA3.1 (Invitrogen) treated with EcoRI and NotI restriction enzymes (hereinafter referred to as mouse MRAP2/pcDNA3.1). Owing to the use of the vector, mouse MRAP2 protein is produced in a mammalian cell.

To the plasmid DNA (100 µg) prepared above, 50 µg of gold particles (Bio Rad), spermidine (100 µl) (SIGMA) and 1M $CaCl_2$ (100 µl (SIGMA)) were added. The mixture was stirred by a vortex and allowed to stand for 10 minutes at room temperature (hereinafter referred to as "gold-DNA particles"). After centrifugation at 3000 rpm for one minute, the supernatant was discarded, followed by washing the pellet three times with 100% ethanol (WAKO). To the gold-DNA particles, 100% ethanol (6 ml) was added, and the mixture was stirred sufficiently by a vortex. The gold-DNA particles were poured in Tefzel Tubing (Bio Rad) to precipitate them on its wall. The Tefzel Tubing with attached gold-DNA particles was dried in the air by removing ethanol and thereafter cut into pieces having a length suitable for use in gene gun (hereinafter referred to as mouse MRAP2/tube).

(2) Antitumor Effect of Mouse MRAP2 by DNA Vaccine Method-1

Five A/J mice (7 weeks old, male, purchased from Japan SLC, Inc.) were used. The tube (mouse MRAP2/tube) prepared above was immobilized on a gene gun. A DNA vaccine was percutaneously administered to the shaved peritoneal cavity of mice with the help of pure helium gas at a pressure of 400 psi three times in total every 7 days (plasmid DNA inoculation amount: 2 µg/animal). After the percutaneous administration, the mouse leukemia cell line EL4 cells, which were found to express the MRAP2 gene in Example 1, were grafted to each mouse to evaluate the antitumor effect (referred to as a prevention model). For the control, the plasmid DNA without inserted mouse MRAP2 gene was administered to 5 mice in the prevention model.

The antitumor effect was evaluated for the size of a tumor (long diameter x (short diameter)$^2$/2) and the rate of surviving mice. As the result, in the prevention model, the tumor sizes after 28 days of the control group and the mouse MRAP2 plasmid administration group were 1359 $mm^3$ and 601 $mm^3$, respectively. Thus, it was found that the tumor size was significantly reduced in the mouse MRAP2 plasmid administration group. As the result that the survival situation was observed in the prevention model, the whole cases of the control group died 61 days after administration; whereas in the mouse MRAP2 plasmid administration group, 60% of the mice were alive. From these results, the significant antitumor effect on the mouse MRAP2 plasmid administration group compared to the control group was demonstrated.

(3) Antitumor Effect of Mouse MRAP2 by DNA Vaccine Method—2

Five A/J mice (7 weeks old, male, purchased from Japan SLC, Inc.) were used. The tube (mouse MRAP2/tube) prepared above was immobilized on a gene gun. A DNA vaccine was percutaneously administered to the shaved peritoneal cavity of mice with the help of pure helium gas at a pressure of 400 psi three times in total every 7 days (plasmid DNA inoculation amount: 2 μg/animal). After the percutaneous administration, the mouse melanoma cell line B16 cells, which were found to express the MRAP2 gene in Example 1, were grafted to each mouse to evaluate the antitumor effect (referred to as a prevention model). For the control, the plasmid DNA without inserted mouse MRAP2 gene was administered to 5 mice in the prevention model group.

The antitumor effect was evaluated for the size of a tumor (long diameter×(short diameter)$^2$/2) and the rate of surviving mice. As the result, in the prevention model, the tumor sizes after 28 days of the control group and the mouse MRAP2 plasmid administration group were 936 mm$^3$ and 483 mm$^3$, respectively. Thus, it was found that the tumor size was significantly reduced in the mouse MRAP2 plasmid administration group. As the result that the survival situation was observed in the prevention model, the whole cases of the control group died 68 days after administration; whereas in the mouse MRAP2 plasmid administration group, 60% of the mice were alive. From these results, the significant antitumor effect on the mouse MRAP2 plasmid administration group compared to the control group was demonstrated.

(4) Preparation of Recombinant Vector Expressing Human MRAP2 In Vivo

A recombinant vector expressing human MRAP2 in vivo was prepared based on the nucleotide sequence represented by SEQ ID NO: 1 in accordance with the following method. PCR was carried out as follows. A reaction mixture was prepared by adding reagents: cDNAs (1 μL), which was prepared from the human leukemia cell line K562 (purchased from ATCC) whose expression was observed in Example 1, two types of primers (0.4 μM for each) having EcoRI and NotI restriction enzyme cleaved sequences (represented by SEQ ID NOs: 19 and 20), 0.2 mM dNTPs, and 1.25 U PrimeSTAR HS polymerase (Takara Shuzo Co., Ltd.), and the attached buffer so as to obtain a total amount of 50 μL; and subjected to PCR using a Thermal Cycler (BIO RAD). In the PCR, 30 cycles were repeated wherein one cycle consists of the treatments: at 98° C. for 10 seconds; at 55° C. for 15 seconds; and at 72° C. for 1 minute. The above-mentioned two types of primers were used for amplifying a region encoding a full-length amino acid sequence represented by SEQ ID NO: 2. After the PCR, the amplified DNA was electrophoresed on 1% agarose gel, and a DNA fragment of approximately 600 bp was purified by use of QIAquick Gel Extraction Kit (QIAGEN).

The purified DNA fragment was ligated to the cloning vector pCR-Blunt (Life Technology), which vector was then transformed into *E. coli* cells, followed by collecting the plasmid vector. By its sequencing, it was confirmed that the sequence of the amplified gene fragment was identical with a desired sequence. The plasmid whose sequence was identical with the desired sequence was treated with EcoRI and NotI restriction enzymes. After purification was carried out with QIAquick Gel Extraction Kit, the desired gene sequence was inserted into the mammalian expression vector pcDNA3.1 (Invitrogen) treated with EcoRI and NotI restriction enzymes (hereinafter referred to as human MRAP2/pcDNA3.1). Owing to the use of the vector, human MRAP2 protein is produced in a mammalian cell.

To plasmid DNA (100 μg) prepared above, 50 μg of gold particles (Bio Rad), spermidine (100 μl) (SIGMA) and 1 M CaCl$_2$ (100 μl (SIGMA)) were added. The mixture was stirred by a vortex and allowed to stand for 10 minutes at room temperature (hereinafter referred to as gold-DNA particles). After centrifugation at 3000 rpm for one minute, the supernatant was discarded, followed by washing the pellet three times with 100% ethanol (WAKO). To the gold-DNA particles, 100% ethanol (6 ml) was added, and the mixture was stirred sufficiently by a vortex. The gold-DNA particles were poured in Tefzel Tubing (Bio Rad) to precipitate them on its wall. The Tefzel Tubing with attached gold-DNA particles was dried in the air by removing ethanol and thereafter cut into pieces having a length suitable for use in gene gun (hereinafter referred to as human MRAP2/tube).

(5) Establishment of Cells Stably Expressing Full-Length Human MRAP2

Human MRAP2/pcDNA3.1 prepared above was introduced by the lipofection method into mouse neuroblastoma cell line N2a cells (ATCC), and then, selection was performed using 500 μg/ml G418 (Nacalai Tesque, Inc.) to establish a N2a cell line stably expressing full-length human MRAP2 (N2a-human MRAP2). Cells obtained by introducing an expression vector (hereinafter referred to as emp/pcDNA3.1) without inserted cDNA encoding human MRAP2 and then performing selection in the same manner as described above were used as control cells (hereinafter referred to as N2a-emp).

(6) Antitumor Effect of Human MRAP2 by DNA Vaccine Method

Five A/J mice (7 weeks old, male, purchased from Japan SLC, Inc) were used. The tube (human MRAP2/tube) prepared above was immobilized on a gene gun. A DNA vaccine was percutaneously administered to the shaved peritoneal cavity of mice with the help of pure helium gas at a pressure of 400 psi three times in total every 7 days (plasmid DNA inoculation amount: 2 μg/animal). After the percutaneous administration, N2a-human MRAP2 or N2a-emp as control cells prepared above was grafted to each mouse to evaluate the antitumor effect (referred to as a prevention model). For the control, the plasmid DNA without inserted human MRAP2 gene was administered to 5 mice in the prevention model.

The antitumor effect was evaluated for the size of a tumor (long diameter×(short diameter)$^2$/2) and the rate of surviving mice. As the result, in the prevention model of N2a-human MRAP2, the tumor sizes after 28 days of the control group and the human MRAP2 plasmid administration group were 1379 mm$^3$ and 513 mm$^3$, respectively. Thus, it was found that the tumor size was significantly reduced in the human MRAP2 plasmid administration group. As the result that the survival situation was observed in the prevention model, the whole cases of the control group died 61 days after administration; whereas in the human MRAP2 plasmid administration group, 60% of the mice were alive. From these results, the significant antitumor effect on the human MRAP2 plasmid administration group compared to the control group was demonstrated in the prevention model of N2a-human MRAP2. On the other hand, no significant antitumor effect on the human MRAP2 plasmid administration group compared to the control group was demonstrated in the prevention model of N2a-emp.

INDUSTRIAL APPLICABILITY

The present invention provides an immunity-inducing agent comprising a polypeptide exhibiting an antitumor activity to cancers and thus is useful for treating and/or preventing cancers.

All publications, patents and patent applications cited herein are incorporated by reference in their entirety.

The invention claimed is:

1. A method for inducing immunity to treat a MRAP2 expressing cancer in a subject in need thereof, comprising administering, to the subject
a polypeptide consisting of the full-length sequence of the amino acid sequence represented by SEQ ID NO: 2, 4, 6, or 8, or a recombinant vector comprising a polynucleotide encoding said polypeptide and capable of expressing said polypeptide in vivo;
wherein said polypeptide has immunity-inducing activity; and
wherein the MRAP2 expressing cancer is leukemia, malignant lymphoma, lung cancer, brain tumor, colon cancer, melanoma, neuroblastoma, pancreatic cancer, stomach cancer, liver cancer, ovarian cancer, esophageal cancer, kidney cancer, mastocytoma or perianal adenocarcinoma.

* * * * *